United States Patent
Kleemann

(10) Patent No.: US 7,381,841 B2
(45) Date of Patent: Jun. 3, 2008

(54) PENTAFLUOROSULFANYLPHENYL-SUBSTITUTED BENZOYLGUANIDINES, PROCESSES FOR THEIR PREPARATION, THEIR USE AS MEDICAMENT OR DIAGNOSTIC AID, AND MEDICAMENT COMPRISING THEM

(75) Inventor: Heinz-Werner Kleemann, Bischofsheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 270 days.

(21) Appl. No.: 10/918,902

(22) Filed: Aug. 16, 2004

(65) Prior Publication Data

US 2005/0043401 A1 Feb. 24, 2005

Related U.S. Application Data

(60) Provisional application No. 60/534,311, filed on Jan. 5, 2004.

(30) Foreign Application Priority Data

Aug. 22, 2003 (DE) ................ 103 38 554

(51) Int. Cl.
*C07C 233/165* (2006.01)
*A61K 31/65* (2006.01)
(52) U.S. Cl. ............ 564/162; 564/134; 514/617; 514/619
(58) Field of Classification Search .......... 564/162, 564/134; 514/618, 617, 619
See application file for complete search history.

(56) References Cited

U.S. PATENT DOCUMENTS

| 5,571,842 A | 11/1996 | Kleemann et al. |
| 5,591,754 A | 1/1997 | Lang |
| 6,057,322 A | 5/2000 | Kleemann et al. |
| 2003/0216476 A1* | 11/2003 | Kleemann ............ 514/618 |

FOREIGN PATENT DOCUMENTS

| DE | 10024319 | 11/2001 |
| WO | WO 00/30624 | 6/2000 |

OTHER PUBLICATIONS

Golub et al, Science, vol. 286, 1999, pp. 531-537.*
U.S. Appl. No. 10/429,810, filed May 5, 2003, Kleemann.
Rundel, W., Notiz uber die Darstellung tert.-butylierter Thiophenole, Diphenyldisulfide und Thianthrene, Chem. Ber.; 101; 1968; pp. 2956-2962.
U.S. Appl. No. 10/452,558, filed Jun. 2, 2003, Kleemann.
U.S. Appl. No. 08/592,699, filed Jan. 26, 1998, Kleemann.
Asaumi, J., et al., Influence of Cell Membrane Potential, and Selectivity of the Na+/H+ Exchanger and Cl-/HCO3 Exchanger on the Intracellular Accumlation of Adriamycin, Anticancer Research 16:725-728 (1996).
Bak, M., et al., Contribution of Na+/H+ exchange to Na+ overload in the ischemic hypertrophied hyperthyroid rat heart, Cardiovascular Research 57 (2003) 1004-1014.
Bonnet, U., et al., Transmembrane acid-extrusion mechanisms: a target for neuropsychopharmacological drug design, Pharmacopsychiat. 30 (1997) 20th Symposium of AGNP Nuremberg 1997.
Bray, P., et al., Na+/H+ Antiporter Chloroquine Uptake and Drug Resistance Inconsistencies in a Newly Proposed Model, Parasitology Today (1999) 15(9) 360-363.

(Continued)

*Primary Examiner*—Shailendra Kumar
(74) *Attorney, Agent, or Firm*—Jiang Lin; Robert Kajubi; Raymond S. Parker, III

(57) ABSTRACT

Pentafluorosulfany0lphenyl-substituted benzoylguanidines, process for their preparation, theie use as medicament or diagnostic aed, and medicament comprising them Pentafluorosulfany0lphenyl-substituted benzoylguanidines of the formulae I and II

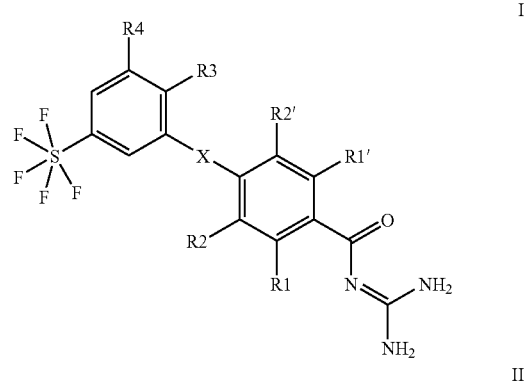

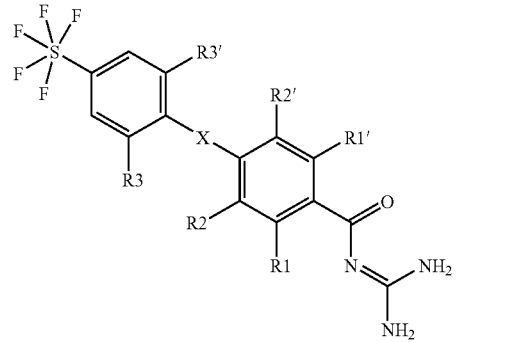

in which R1, R1', R2, R2', R3, R3', R4 and X have the meanings indicated in the claims, are suitable as antiarrhythmic medicaments with a cardioprotective component for the prophylaxis of infarction and treatment of infarction and for the treatment of angina pectoris. They also inhibit preventively the pathophysiological processes associated with the development of ischemia-induced damage, especially in the triggering of ischemia-induced cardiac arrhythmias.

10 Claims, 1 Drawing Sheet

OTHER PUBLICATIONS

Figure 1:
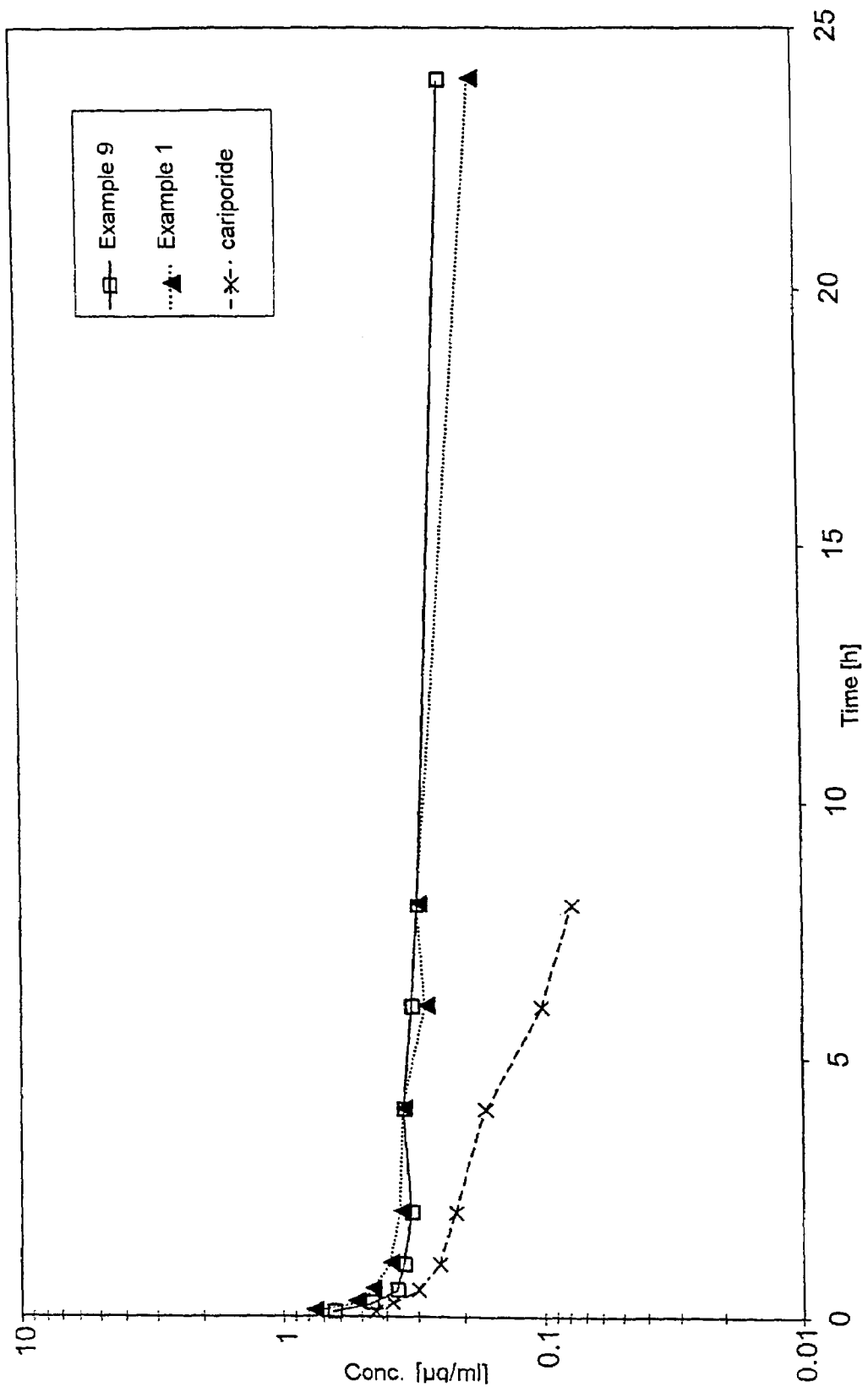

Carini, R., et al., Ethanol Potentiates Hypoxic Liver Injury Role of Hepatocyte Na+ Overload, Biochimica et Biophysica Acta 1502 (2000) 508-514.

Engelhardt, S., et al., Inhibition of Na+/H+ Exchanger Prevents Hypertrophy, Fibrosis, and Heart Failure in Beta1-Adrenergic Receptor Transgenic Mice, Circulation Research (2002) 90(7) 814-819.

Forestal, et al., Different effect of cold storage and rearming on three pH regulating transporters in isolated rat hepatocytes, Am. J. Physiol (1997) 272(3, Pt. 1) G638-G645.

Gumina, R., et al., Na+/H+ exchange inhibition prevents endothelial dysfunction after I/R injury, Am. J. Physiol Heart Circ. Physiol (2001) 281: H1260-H1266.

Harper, S., 431-441, Inhibition of Na+/H+ exchange perserves viability, restores mechanical function, and prevents the pH paradox in reperfusion injury to rat neonatal myocytes, Basic Research in Cardiology 88:430-442 (1993).

He, H., et al., Change of sodium-hydrogen exchanger mRNA expression in lung patients with pulmonary hypertension and its clinical significance, Dier Junyl Daxue Xuebao (2002) 23(2) 193-195.

Horikawa, N., et al., Na+/H+ Exchange Inhibitor SM-20220 Improves Endothelial Dysfunction Induced by Ischemia-Reperfusion, Jpn. J. Pharmacol. 85, 271-277 (2000).

Jandeleit-Dahm, K., et al., Diabetes-Induced Vascular Hypertrophy is a Accompanied by Activation of Na+ -H+ Exchange and Prevented by Na+ -H+ Exchange Inhibition, Circulation Research (2000) 87(12) 1133-1140.

Karmazyn, M, Antiarrhythmic Effects of Na-H Exchange Inhibition, Drug Development Research (2000) 55:22-28.

Karmazyn, M, Therapeutic Potential of Na-H Exchange Inhibitors for the Treatment of Heart Failure, Exp. Opin. Invest. Drugs (2001) 10(5) 835-843.

Karmazyn, M, et al., Comparative Effects of Na+/H+ Exchange Inhibitors Against Cardiac Injury Produced by Ischemia-Reperfusion, Hypoxia/Reoxygenation, and the Calcium Paradox, Journal, of Cardiovascular Pharmacology (1993) 21:172-178.

Karmazyn, M., et al., The Sodium-Hydrogen Exchanger From Molecule to Its Role in Disease, Kluwer Academic Publishers (2003) some chapters.

Karmazyn, Morris, Na+/H+ exchange inhibitors reverse lactate-induced depression in postischaemic ventricular recovery, Br. J. Pharmacol. (1993), 108, 50-56.

Karuri, A., et al., Selective Cellular acidification and toxicity of weak organic acids in an acidic microenvironment, Br. J. Cancer (1993) 68, 1080-1087.

Kim, Y., et al., Na+/H+ Exchange Inhibition Improves Long-Term Myocardial Preservation, Ann. Thorac. Surg. 66(2):436-442 (Aug. 1998).

Kim, Y., et al., Na+/H+ exchange inhibition improves post-transplant myocardial compliance in 4-hour stored donor hearts, Cadiovascular Surgery, vol. 6 No. 1 pp. 67-75 (1998).

Koike, T., et al., Sodium overload through voltage-dependent Na+ channels induces necrosis and apoptosis of rat superior cervical ganglion cells in vitro, Brain Research Bullentin (2000) vol. 51 (4) 345-355.

Koren, W., et al., Amiloride-sensitive Na+/H+ exchange in erythrocytes of patients with NIDDM: a prospective study, Diabetologia (1997) 40:302-306.

Krump, E., et al., Induction of Tyrosine Phosphorylation and Na+/H+ Exchanger Activation during Shrinkage of Human Neutrophils, Journal of Biological Chemistry (1997), 272(28) 17303-17311.

Kusumoto, K., et al., Na+/H+ exchange inhibition reduces hypertrophy and heart failure after myocardial infarction in rats, Am J. Physiol Heart Circ Physiol (2001) 280: H738-H745.

Liu, L, et al., The effects of cariporide against atheroscierosis induced by high lipid diet in rabbits., Zhongguo Dongmal Yinghua Zazhi (2002) 10(1) 1-5.

Linz, W., et al., Long-Term Treatment with the NHE-1 Inhibitor Cariporide Extends The Normal Lifespan of Wistar Kyoto Rats, Achives of Pharmacology Supplemental to vol. 363 (4) (2001) Abstract 12.

Nemeth, Z., et al., NHE blockade inhibits chemokine production and NF-kB activation in immunostimulated endothelial cells, Am J Physiol Cell Physiol (2002) 283 C396-C403.

Nemeth, Z., et al., Na+/H+ exchanger blockade inhibits entercyte inflammatory response and protects against colitis, Am J Physiol Gastrointest Liver Physiol (2002) 283: G122-G132.

Pang, T., et al., Expression of Calcineurin B Homologous Protein 2 Protects Serum Deprivation-induced Cell Death by Serum-independent Activation of Na+/H+ Exchanger, The Journal of Biological Chemistry (2002) vol. 277 (46) 43771-43777.

Reshkin, S., et al., Na+/H+ exchanger-dependent intracellular alkalinization is an early event in malignant transformation and plays an essential role in the development of subsequent transformation-associated phenotypes, FASEB Journal (2000) vol. 14 2185-2197.

Reshkin, S., et al., Paclitaxel Induces Apoptosis via Protein Kinase A- and p38 Mitogent-activated Protein-dependent inhibition of the Na+/H+ Exchanger (NHE) Isoform 1 in Human Breast Cancer Cells, Clinical Cancer Research (Jun. 2003) vol. 9, 2366-2373.

Rich, I., et al., Apoptosis of leukemic cells accompanies reduction in intracellular pH after targeted inhibition of the Na+/H+ exchanger, Blood (Feb. 2000) vol. 95 (4) 1427-1434.

Sack, S., et al., Inhibition of Na+/H+ Exchange Prevents Ventricular Fibrillation and Perserves Function in Porcine Stunned Myocardium, J. Mol Cell Cardiol 24 (Supplement I) (1992).

Sanchez, C., et al, Is The Putative Chloroquine Resistance Mediator CG2 the Na+/H+ Exchanger of Plasmodium Falciparum?, Cell (1998) vol. 92 601-602.

Scholz, W., et al., Na+/H+ exchange and its inhibition in cardiac ischemia and reperfusion, Basic Res Cardiol 88:443-455 (1993).

Scholz, et al., Hoe 694, a new Na+/H+ exchange inhibitor and its effects in cardiac ischaemia, Br. J. Pharmacol (1993) 109 562-568.

Shen, M., et al., Anion exchanger isoform 2 operates un parallel with Na+/H+ exchanger isoform 1 during regulatory vol. decrease of human cervical cancer cells, FEBS Letters 512 (2002) 52-58.

Telejko, B, The Role of Na+/H+ exchangers in the pathogenesis of arterial hypertension and vascular complications of disease mellitus., Diabetologia (2002) vol. 45 (Supplement 2) Abstract 375.

Tu, J., et al., Protective effect of Na+/H+ exchanger inhibitor cariporide on the injury of vascular endothelial function induced by hypercholesterolemia, Hunan Yike Daxue Xuebao (2002) 27(1) 13-16 Abstract.

Wu, B., et a., The Role of G Protein, Protein Kinase C and Na+ -H+ Exchanger in Endothelial-1 Induced Cardiomyocyte Hypertrophic Responses, Acta Physiologica Sinica (Feb. 1998) 50 (1) 87-93.

Wu, G., et al., Induction of the acidification and apoptosis of human lung cancer cell line throught inhibition of Na+/H+ exchanger-1 with dimethyl amiloride, Di-San Junyi Daxue Xuebao (1998) 20 (16) 476-479 (Abstract only).

Wuensch, S., et al., Differential Stimulation of the Na+/H+ Exchanger Determines Chloroquine Uptake in Plasmodium Falciparum, Journal of Cell Biology (1998) 140(2) 335-345.

Yamazaki, T., et al., Role of Ion Channels and Exchangers in Mechanical Stretch-Induced Cardiomyocyte Hypertrophy, Circ. Res. (1998) 82(4) 430-437.

Yasutake, M., et al., Na+/H+ exchange and reperfusion arrhythmias: protection by intracoronary infusion of a novel inhibitor, Am. J. Physiol (1994) 267 (Nr. 6) Pt. 2: H2430-H2440.

Yoshida, H., et al., Na+/H+ exchange inhibition attenuates hypertrophy and heart failure in 1-wk postinfarction rat myocardium, Am. J. Physiol Heart Circ. Physiol (2000) 278: H300-H304.

* cited by examiner

PENTAFLUOROSULFANYLPHENYL-SUBSTITUTED BENZOYLGUANIDINES, PROCESSES FOR THEIR PREPARATION, THEIR USE AS MEDICAMENT OR DIAGNOSTIC AID, AND MEDICAMENT COMPRISING THEM

This application claims the benefit of U.S. Provisional Application No. 60/534,311, filed Jan. 5, 2004.

The invention relates to pentafluorosulfanylphenyl-substituted benzoylguanidines of the formulae I and II

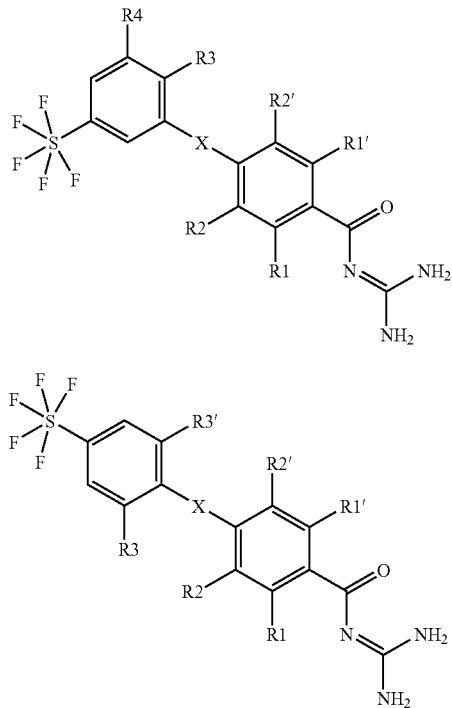

in which the meanings are

R1 and R1' independently of one another hydrogen, alkyl having 1, 2, 3 or 4 carbon atoms, alkoxy having 1, 2, 3 or 4 carbon atoms, F, Cl, Br, I, —CN, NR5R6, —$O_a$—$(CH_2)_b$—$(CF_2)_c$—$CF_3$ or —$(SO_d)_e$—$(CH_2)_f$—$(CF_2)_g$—$CF_3$;

R5 and R6 independently of one another hydrogen, alkyl having 1, 2, 3 or 4 carbon atoms or —$CH_2$—$CF_3$;

d zero, 1 or 2;

a, b, c, e, f and g independently of one another zero or 1;

R2 and R2' independently of one another hydrogen, F, Cl, Br, I, —CN, —$SO_2CH_3$, alkoxy having 1, 2, 3 or 4 carbon atoms, NR5R6, —$O_a$—$(CH_2)_b$—$(CF_2)_c$—$CF_3$, —$(SO_h)_k$—$(CH_2)_l$—$(CF_2)_m$—$CF_3$, alkyl having 1, 2, 3, 4, 5 or 6 carbon atoms, cycloalkyl having 3, 4, 5, 6, 7 or 8 carbon atoms, in which 1, 2, 3 or 4 hydrogen atoms may be replaced by fluorine atoms, —$(CH_2)_n$-phenyl which is unsubstituted or substituted by 1, 2 or 3 radicals selected from the group consisting of F, Cl, Br, I, —$O_o$—$(CH_2)_p$—$CF_3$, alkoxy having 1, 2, 3 or 4 carbon atoms, alkyl having 1, 2, 3 or 4 carbon atoms and —$SO_2CH_3$, or —$(CH_2)_q$-heteroaryl which is unsubstituted or substituted by 1, 2 or 3 radicals selected from the group consisting of F, Cl, Br, I, —$O_r$—$(CH_2)_s$—$CF_3$, alkoxy having 1, 2, 3 or 4 carbon atoms, alkyl having 1, 2, 3 or 4 carbon atoms and —$SO_2CH_3$;

R5 and R6 independently of one another hydrogen, alkyl having 1, 2, 3 or 4 carbon atoms or —$CH_2$—$CF_3$;

a, b and c independently of one another zero or 1;

h zero, 1 or 2;

k zero or 1;

l zero, 1, 2, 3, or 4;

m and o independently of one another zero or 1;

p zero, 1, 2 or 3;

n zero, 1, 2, 3 or 4;

r zero or 1;

s zero, 1, 2 or 3;

q zero, 1, 2, 3, or 4;

R3 and R3' independently of one another hydrogen, F, Cl, Br, I, —CN, —$SO_2CH_3$, alkyl having 1, 2, 3, 4, 5 or 6 carbon atoms, alkoxy having 1, 2, 3, or 4 carbon atoms or —$O_t$—$(CH_2)_u$—$CF_3$;

t zero or 1;

u zero, 1, 2 or 3;

R4 hydrogen, F, Cl, Br, I, —CN, —$SO_2CH_3$, NR5R6, —$(SO_v)_w$—$(CH_2)_x$—$(CF_2)_y$—$CF_3$, —$O_z$—$(CH_2)_{aa}$—$(CF_2)_{bb}$—$CF_3$, alkyl having 1, 2, 3, 4, 5 or 6 carbon atoms, alkoxy having 1, 2, 3 or 4 carbon atoms or cycloalkyl having 3, 4, 5, 6, 7 or 8 carbon atoms, in which 1, 2, 3 or 4 hydrogen atoms may be replaced by fluorine atoms;

R5 and R6 independently of one another hydrogen, alkyl having 1, 2, 3 or 4 carbon atoms or —$CH_2$—$CF_3$;

v zero, 1 or 2;

x zero, 1, 2, 3 or 4;

w, y, z, aa and bb independently of one another zero or 1;

or

R4 —$(CH_2)_{cc}$-phenyl which is unsubstituted or substituted by 1, 2, or 3 radicals selected from the group consisting of F, Cl, Br, I, —$O_{dd}$—$(CH_2)_{ee}$—$CF_3$, alkoxy having 1, 2, 3 or 4 carbon atoms, alkyl having 1, 2, 3 or 4 carbon atoms and —$SO_2CH_3$;

dd zero or 1;

ee zero, 1, 2 or 3;

cc zero, 1, 2, 3 or 4;

or

R4 —$(CH_2)_{ff}$-heteroaryl which is unsubstituted or substituted by 1, 2 or 3 radicals selected from the group consisting of F, Cl, Br, I, —$O_{gg}$—$(CH_2)_{hh}$—$CF_3$, alkoxy having 1, 2, 3 or 4 carbon atoms, alkyl having 1, 2, 3 or 4 carbon atoms and —$SO_2CH_3$;

gg zero or 1;

hh zero, 1, 2 or 3;

ff zero, 1, 2, 3 or 4;

X a direct linkage, O, NR7, $S(O)_{kk}$;

R7 hydrogen, alkyl having 1, 2, 3 or 4 carbon atoms, —$(CH_2)_{mm}$—$CF_3$ or —$SO_2CH_3$ kk zero, 1 or 2;

mm zero, 1, 2 or 3;

where —$O_a$—$(CH_2)_b$—$(CF_2)_c$—$CF_3$ in the definitions of R1 and R1' and R2 and R2' can be selected independently of one another, where NR5R6 in the definitions of R1 and R1', R2 and R2' and R4 can be selected independently of one another, and the pharmaceutically acceptable salts thereof.

Preference is given to compounds of the formulae I and II in which the meanings are:

R1 and R1' independently of one another hydrogen, alkyl having 1, 2, 3 or 4 carbon atoms, methoxy, ethoxy, F, Cl, NR5R6, —O—CH$_2$—CF$_3$ or —(SO$_d$)$_e$—(CH$_2$)$_f$—CF$_3$;

R5 and R6 independently of one another hydrogen, alkyl having 1, 2, 3 or 4 carbon atoms or —CH$_2$—CF$_3$;

d zero, 1 or 2;

e and f independently of one another zero or 1;

R2 and R2' independently of one another hydrogen, F, Cl, —SO$_2$CH$_3$, —(SO$_h$)$_k$—(CH$_2$)$_l$—CF$_3$, alkyl having 1, 2, 3 or 4 carbon atoms, cycloalkyl having 3, 4, 5, 6 or 7 carbon atoms, in which 1, 2, 3 or 4 hydrogen atoms may be replaced by fluorine atoms, phenyl which is unsubstituted or substituted by 1-2 radicals selected from the group consisting of F, Cl, —O$_o$—(CH$_2$)$_p$—CF$_3$, methoxy, ethoxy, alkyl having 1, 2, 3 or 4 carbon atoms and —SO$_2$CH$_3$, or heteroaryl which is unsubstituted or substituted by 1-2 radicals selected from the group consisting of F, Cl, —O$_r$—(CH$_2$)$_s$—CF$_3$, methoxy, ethoxy, alkyl having 1, 2, 3 or 4 carbon atoms and —SO$_2$CH$_3$;

h zero, 1 or 2;

k zero or 1;

l zero, 1, 2, 3, or 4;

o zero or 1;

p zero, 1, 2 or 3;

r zero or 1;

s zero, 1, 2 or 3;

R3 and R3' independently of one another hydrogen, Ff, Cl, —SO$_2$CH$_3$, alkyl having 1, 2, 3 or 4 carbon atoms, methoxy, ethoxy or —O$_t$—(CH$_2$)$_u$—CF$_3$, t zero or 1;

u zero, 1, 2 or 3;

R4 hydrogen, F, Cl, —SO$_2$CH$_3$, —(SO$_v$)$_w$—(CH$_2$)$_x$—CF$_3$, —O$_z$—(CH$_2$)$_{aa}$—CF$_3$, alkyl having 1, 2, 3 or 4 carbon atoms, methoxy, ethoxy or cycloalkyl having 3, 4, 5, 6 or 7 carbon atoms, in which 1, 2, 3 or 4 hydrogen atoms may be replaced by fluorine atoms;

v zero, 1 or 2;

w, x, z and aa independently of one another zero or 1;

or

R4 phenyl which is unsubstituted or substituted by 1-2 radicals selected from the group consisting of F, Cl, —O$_{dd}$—(CH$_2$)$_{ee}$—CF$_3$, methoxy, ethoxy, alkyl having 1, 2, 3 or 4 carbon atoms and —SO$_2$CH$_3$;

dd and ee independently of one another zero or 1;

or

R4 heteroaryl which is unsubstituted or substituted by 1-2 radicals selected from the group consisting of F, Cl, —O$_{gg}$—(CH$_2$)$_{hh}$—CF$_3$, methoxy, ethoxy, alkyl having 1, 2, 3 or 4 carbon atoms and —SO$_2$CH$_3$;

gg and hh independently of one another zero or 1;

X a direct linkage, O, NR7, S(O)$_{kk}$;

R7 hydrogen, alkyl having 1, 2, 3 or 4 carbon atoms, —CH$_2$—CF$_3$ or —SO$_2$CH$_3$;

kk zero, 1 or 2;

and the pharmaceutically acceptable salts thereof.

Particular preference is given to compounds of the formulae I and II in which the meanings are:

R1 and R1' independently of one another hydrogen, alkyl having 1, 2, 3 or 4 carbon atoms, methoxy, ethoxy, F, Cl, NR5R6, —O—CH$_2$—CF$_3$ or —(SO$_d$)$_e$—(CH$_2$)$_f$—CF$_3$;

R5 and R6 independently of one another hydrogen, alkyl having 1, 2, 3 or 4 carbon atoms or —CH$_2$—CF$_3$;

d zero, 1 or 2;

e and f independently of one another zero or 1;

R2 and R2' independently of one another hydrogen, F, Cl, —SO$_2$CH$_3$, —(SO$_h$)$_k$—(CH$_2$)$_l$—CF$_3$, methyl, cycloalkyl having 3, 4, 5, 6 or 7 carbon atoms, in which 1, 2, 3 or 4 hydrogen atoms may be replaced by fluorine atoms, phenyl which is unsubstituted or substituted by a radical selected from the group consisting of F, Cl, —O$_o$—(CH$_2$)$_p$—CF$_3$, methoxy, ethoxy, alkyl having 1, 2, 3 or 4 carbon atoms and —SO$_2$CH$_3$, or heteroaryl which is unsubstituted or substituted by a radical selected from the group consisting of F, Cl, —O$_r$—(CH$_2$)$_s$—CF$_3$, methoxy, ethoxy, alkyl having 1, 2, 3 or 4 carbon atoms and —SO$_2$CH$_3$;

h zero, 1 or 2;

k, l, o, p, r and s independently of one another zero or 1;

R3 and R3' independently of one another hydrogen, F, Cl, —SO$_2$CH$_3$, methyl, methoxy, ethoxy or —O$_t$—(CH$_2$)$_u$—CF$_3$;

t and u independently of one another zero or 1;

R4 hydrogen, F, Cl, —SO$_2$CH$_3$, —(SO$_v$)$_w$—(CH$_2$)$_x$—CF$_3$, —O$_z$—(CH$_2$)$_{aa}$—CF$_3$, methyl, methoxy, ethoxy or cycloalkyl having 3, 4, 5, 6 or 7 carbon atoms, in which 1, 2, 3 or 4 hydrogen atoms may be replaced by fluorine atoms;

v zero, 1 or 2;

w, x, z and aa independently of one another zero or 1;

X a direct linkage, O, NR7 or S(O)$_{kk}$;

R7 hydrogen, methyl, ethyl, —CH$_2$—CF$_3$ or —SO$_2$CH$_3$;

kk zero, 1 or 2;

and the pharmaceutically acceptable salts thereof.

Very particular preference is given to compounds of the formulae I and II, in which the meanings are:

R1 and R1' independently of one another hydrogen, methyl, F, Cl, —CF$_3$ or —O—CH$_2$—CF$_3$;

R2 and R2' independently of one another hydrogen, F, Cl, —SO$_2$CH$_3$, —SO$_2$—CF$_3$, CF$_3$ or methyl;

R3 and R3' independently of one another hydrogen, F, Cl, —SO$_2$CH$_3$, methyl, —CF$_3$ or —O—CH$_2$—CF$_3$;

R4 hydrogen, F, Cl, —SO$_2$CH$_3$, —O—CH$_2$—CF$_3$ or methyl;

X a direct linkage, O, NR7 or S(O)$_{kk}$;

R7 hydrogen, methyl, ethyl, —CH$_2$—CF$_3$ or —SO$_2$CH$_3$;

kk zero, 1 or 2;

and the pharmaceutically acceptable salts thereof.

In one embodiment moreover preference is given to compounds of the formulae I and II in which R1 and R1' are described independently of one another by hydrogen, methyl, F, Cl, —CF$_3$ or —O—CH$_2$—CF$_3$, and particular preference is given to compounds in which R1 and R1' are described independently of one another by hydrogen or methyl, In a further embodiment, preference is given to compounds of the formulae I and II in which R2 and R2' are described independently of one another by hydrogen, F, Cl, —SO$_2$CH$_3$, —SO$_2$CF$_3$, —CF$_3$ or methyl, and particular preference is given to compounds in which R2 and R2' are described independently of one another by hydrogen or —SO$_2$CH$_3$.

In a further embodiment, preference is given to compounds of the formulae I and II in which R3 and R3' are described independently of one another by hydrogen, F, Cl, —SO$_2$CH$_3$, methyl, —CF$_3$ or —O—CH$_2$—CF$_3$, and particular preference is given to compounds in which R3 and R3' are described independently of one another by hydrogen or methyl.

In a further embodiment, preference is given to compounds of the formulae I and II in which R4 is described by hydrogen, F, Cl, —SO$_2$CH$_3$, —O—CH$_2$—CF$_3$ or methyl, and particular preference is given to compounds in which R4 is described by hydrogen.

In a further embodiment, preference is given to compounds of the formulae I and II in which X is a direct linkage or is described by O, NR7 or S(O)$_{kk}$, where R7 is hydrogen, methyl, ethyl, —CH$_2$—CF$_3$ or —SO$_2$CH$_3$, preferably hydrogen or methyl, and where kk is zero, 1 or 2, preferably zero or 2.

Specific preference is given to compounds selected from the group of:
N-[5-Methanesulfonyl-2-methyl-4-(3-pentafluorosulfanylphenoxy)benzoyl]guanidine,
N-[5-Methanesulfonyl-2-methyl-4-(4-pentafluorosulfanylphenoxy)benzoyl]guanidine,
N-[5-Methanesulfonyl-2-methyl-4-(4-pentafluorosulfanylphenylsulfanyl)benzoyl]-guanidine,
N-[5-Methanesulfonyl-2-methyl-4-(4-pentafluorosulfanylphenylsulfonyl)benzoyl]-guanidine,
N-[5-Methanesulfonyl-2-methyl-4-(3-pentafluorosulfanylphenylamino)benzoyl]-guanidine,
N-[5-Methanesulfonyl-2-methyl-4-(4-pentafluorosulfanylphenylamino)benzoyl]-guanidine,
N-{5-Methanesulfonyl-2-methyl-4-[methyl-(3-pentafluorosulfanylphenyl)-amino]benzoyl}guanidine,
N-{5-Methanesulfonyl-2-methyl-4-[methyl-(4-pentafluorosulfanylphenyl)-amino]benzoyl}guanidine,
N-(2-Methanesulfonyl-5-methyl-4'-pentafluorosulfanylbiphenyl-4-carbonyl)guanidine,
N-(2-Methanesulfonyl-5-methyl-3'-pentafluorosulfanylbiphenyl-4-carbonyl)guanidine, and
N-(2-Methanesulfonyl-5,2'-dimethyl-4'-pentafluorosulfanylbiphenyl-4-carbonyl)-guanidine.

If the substituents R1, R1', R2, R2', R3, R3' or R4 contain one or more centers of asymmetry, these may independently of one another have both the S and the R configuration. The compounds may be in the form of optical isomers, of diastereomers, of racemates or of mixtures thereof.

The present invention encompasses all tautomeric forms of the compounds of the formulae I and II.

Alkyl radicals may be straight-chain or branched. This also applies if they carry substituents or occur as substituents of other radicals, for example in fluoroalkyl radicals, alkoxy radicals, fluoroalkoxy radicals, alkylamino radicals, dialkylamino radicals and alkylsulfonyl radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), pentyl and hexyl. Preferred alkyl radicals are methyl, ethyl, n-propyl and isopropyl, particularly preferably methyl and ethyl. One or more, for example 1, 2, 3, 4 or 5, hydrogen atoms in alkyl radicals may be replaced by fluorine atoms. Examples of such fluoroalkyl radicals are trifluoromethyl, 2,2,2-trifluoroethyl and pentafluoroethyl. Substituted alkyl radicals may be substituted in any positions.

Examples of cycloalkyl radicals are cyclopropyl, cyclobutyl, cyclopentyl, cyclohexyl, cycloheptyl or cyclooctyl. One or more, for example 1, 2, 3 or 4, hydrogen atoms in cycloalkyl radicals may be replaced by fluorine atoms. Substituted cycloalkyl radicals may be substituted in any positions.

Phenyl radicals may be unsubstituted or be substituted one or more times, for example once, twice or three times, by identical or different radicals. This likewise applies to phenyl radicals in groups such as, for example, phenylalkyl or phenyloxy. The substituent in monosubstituted phenyl radicals may be in position 2, position 3 or position 4.

Disubstituted phenyl may be substituted in the 2,3 position, 2,4 position, 2,5 position, 2,6 position, 3,4 position or 3,5 position. The substituents in trisubstituted phenyl radicals may be in the 2,3,4 position, 2,3,5 position, 2,4,5 position, 2,4,6 position, 2,3,6 position or 3,4,5 position.

Heteroaryl radicals are aromatic ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Heteroaryl radicals may be unsubstituted or be substituted one or more times, for example once, twice or three times, by identical or different radicals. This applies likewise to heteroaryl radicals such as, for example, in the radical heteroarylalkyl. Examples of heteroaryl are furanyl, thienyl, pyrrolyl, imidazolyl, pyrazolyl, triazolyl, tetrazolyl, oxazolyl, isoxazolyl, oxadiazolyl, thiadiazolyl, thiazolyl, isothiazolyl, pyridyl, pyrazinyl, pyrimidinyl, pyridazinyl, indolyl, benzimidazolyl, indazolyl, quinolyl, isoquinolyl, phthalazinyl, quinoxalinyl, quinazolinyl and cinnolinyl.

Heteroaryl radicals are, in particular, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol -3- or -5-yl, 1,2,3-thiadiazol-4- or -5-yl, 2-, 3- or 4-pyridyl, 2-, 4-, 5- or 6-pyrimidinyl, 3- or 4-pyridazinyl, 2- or 3-pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also encompassed are the corresponding N-oxides of these compounds, i.e. for example 1-oxy-2-, 3- or 4-pyridyl. Particularly preferred heteroaromatic radicals are 2- or 3-thienyl, 2- or 3-furyl, 1-, 2- or 3-pyrrolyl, 1-, 2-, 4- or 5-imidazolyl, 2-, 3-, 4-, 5-, 6-, 7- or 8-quinolyl, 1-, 3-, 4- or 5-pyrazolyl, 2-, 3- or 4-pyridyl, 2- or 3-pyrazinyl, 2-, 4-, 5- or 6-pyrimidinyl and 3- or 4-pyridazinyl.

Patient includes both human and other mammals.

Pharmaceutically effective amount is meant to describe an amount of compound or compounds according to the present invention effective in producing the desired therapeutic effect.

The present invention also relates to the processes described below for preparing the compounds of the formulae I and/or II.

The present invention relates to a process for preparing a compound of the formulae I or II and/or the pharmaceutically acceptable salts thereof in which X is oxygen (scheme 1), which comprises a) reacting a phenol of the formulae III or IV with an aromatic compound of the formula V to give a compound of the formulae VIa or VIIa, and b) reacting a compound of the formulae VIa or VIIa with guanidine to give the acylguanidine of the formulae Ia or IIa,

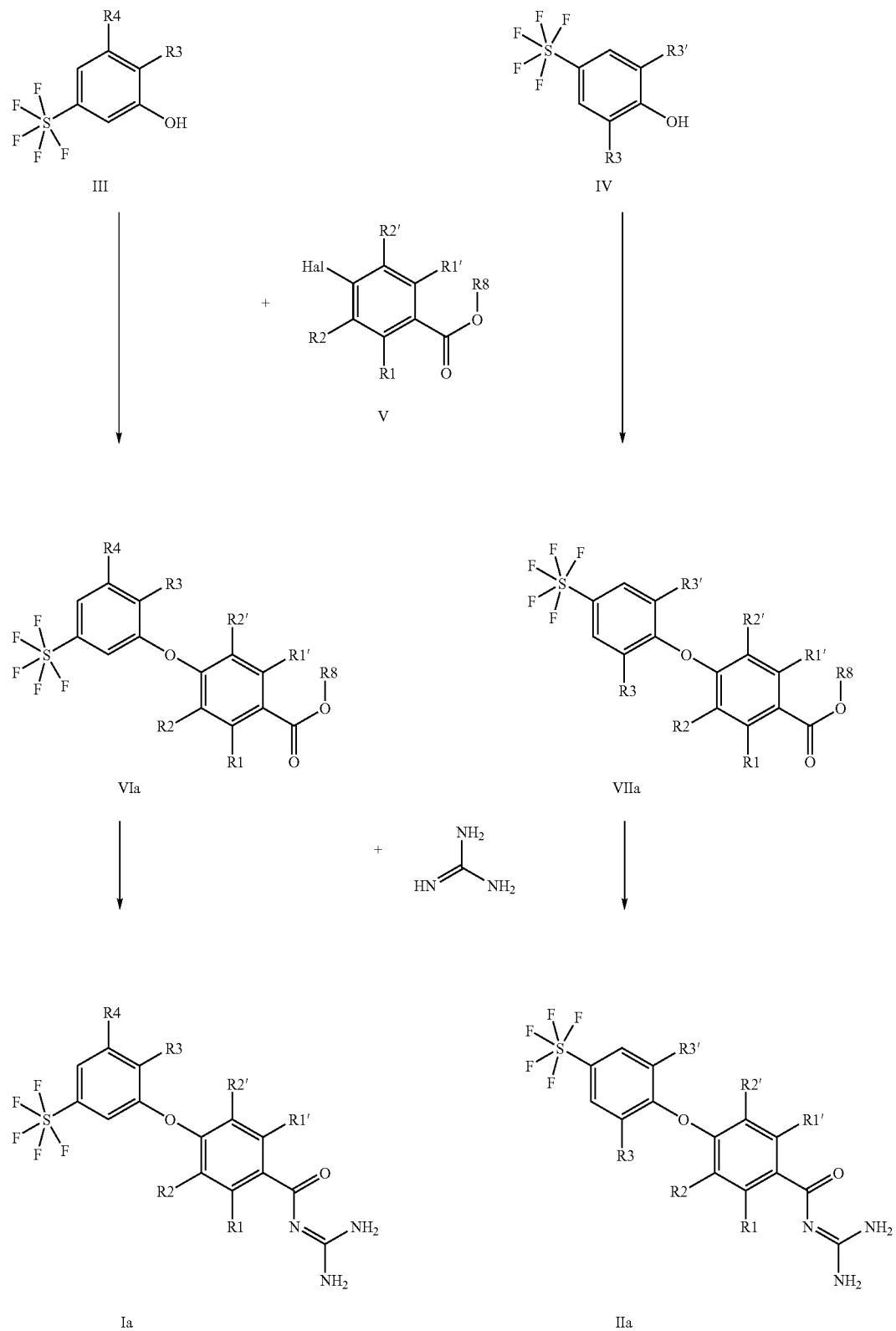

in which R1, R1', R2, R2', R3, R3' and R4 have the meaning indicated above, and in which the meanings are Hal F, Cl, Br or I, R8 hydrogen or alkyl having 1, 2, 3 or 4 carbon atoms.

The phenols of the formulae III or IV are deprotonated in a suitable solvent, preferably in a dipolar aprotic solvent such as, for example, acetonitrile, DMF, NMP or DMSO, with the aid of an inorganic base such as, for example, $K_2CO_3$ or $Cs_2CO_3$, or with the aid of an organic base such as, for example, triethylamine or TBTMG, at a temperature between 0° C. and the boiling point of the solvent used, and then reacted with the electrophilic aromatic compound of the formula V in a nucleophilic aromatic substitution at a temperature between 0° C. and the boiling point of the solvent used, preferably between RT and 150° C., to give compounds of the formulae VIa or VIIa.

The reaction of the compounds of the formulae VIa or VIIa to give the acylguanidines of the formulae Ia or IIa takes place either with free guanidine base or, preferably, with guanidinium chloride which is initially stirred together with KOtBu in an inert solvent, preferably DMF or NMP, and then stirred together with the ester at a temperature between 0° C. and the boiling point of the solvent, preferably between RT and 100° C.

The esters of the formula VIa or VIIa in which R8 is alkyl can also be initially hydrolyzed to the carboxylic acids and then reacted, preferably in the presence of an activating agent, with guanidine to give acylguanidines of the formulae Ia or IIa. The starting compounds of the formulae III, IV and V can be obtained commercially or can be prepared by in analogy to processes known to the skilled worker and described in the literature.

The present invention further relates to a process for preparing a compound of the formula I or II and/or the pharmaceutically acceptable salts thereof, in which X is NR7 (scheme 2), which comprises a) sulfonating an aniline of the formulae VII or IX with a sulfonyl chloride, for example methanesulfonyl chloride, to give a compound of the formulae X or XI, b) reacting the compound of the formulae X or XI with an aromatic compound of the formula V to give a compound of the formulae VIb or VIIb, c) to prepare a compound of the formulae Ib or IIb in which R7 is different from hydrogen, derivatizing a compound of the formulae VIa or VIIb to give a compound of the formulae VIc or VIIc, and d) reacting a compound of the formulae VIb/c or VIIb/c with guanidine to give an acylguanidine of the formulae Ib or IIb Scheme 2 (part 1)

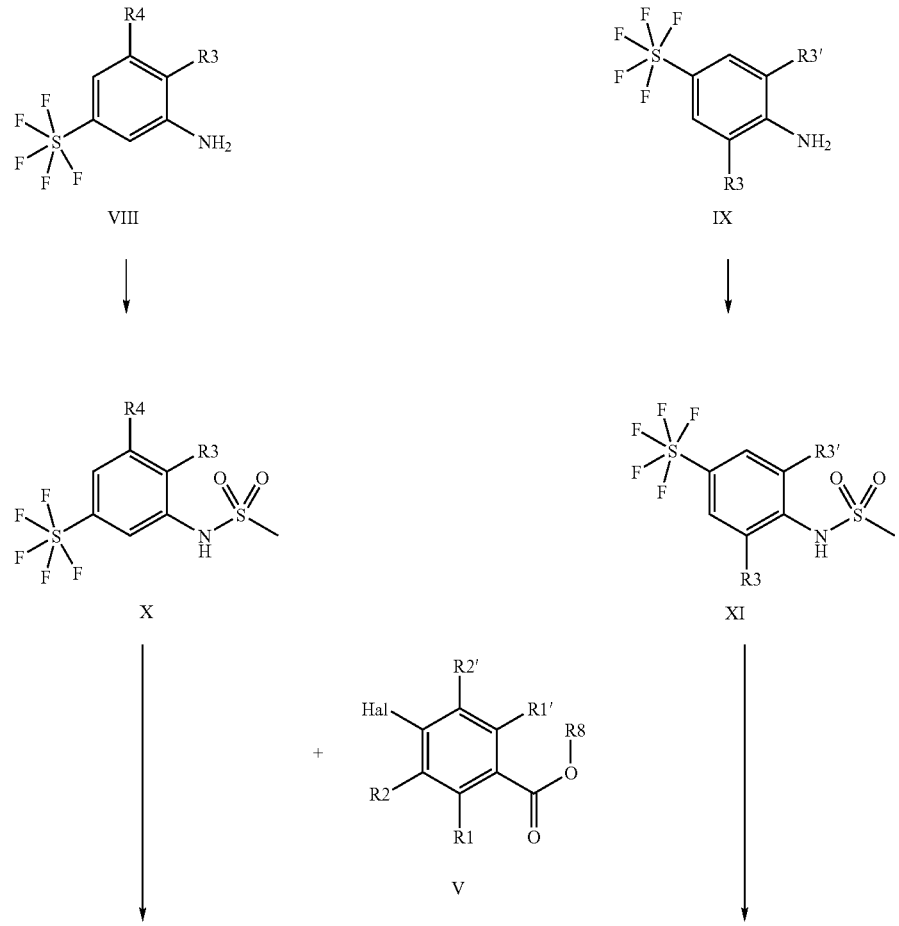

-continued
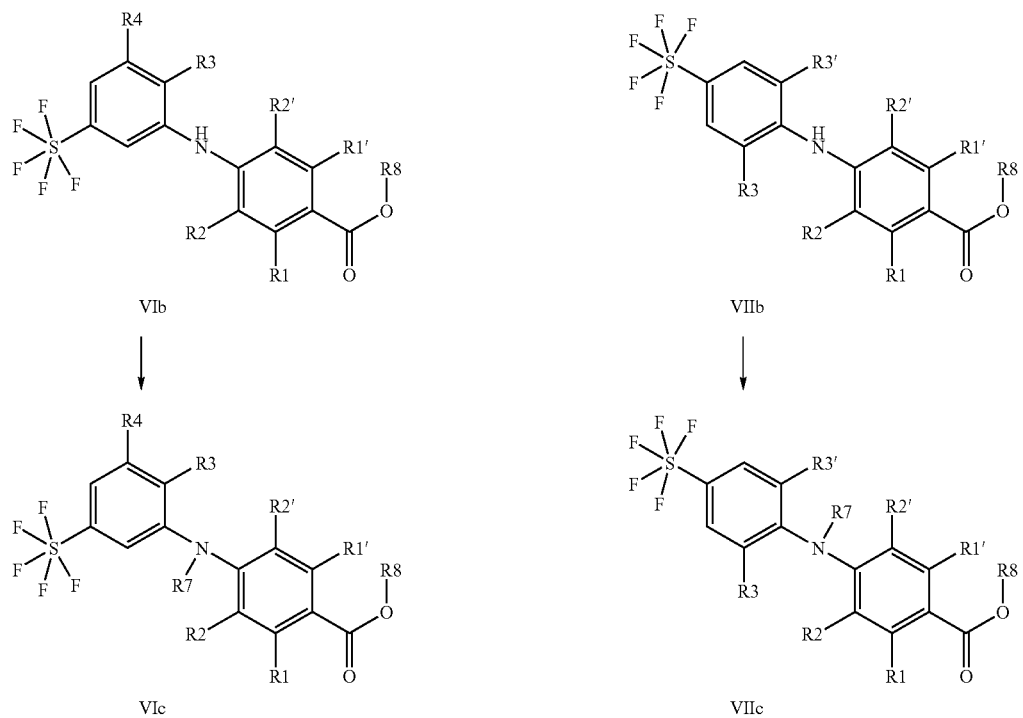
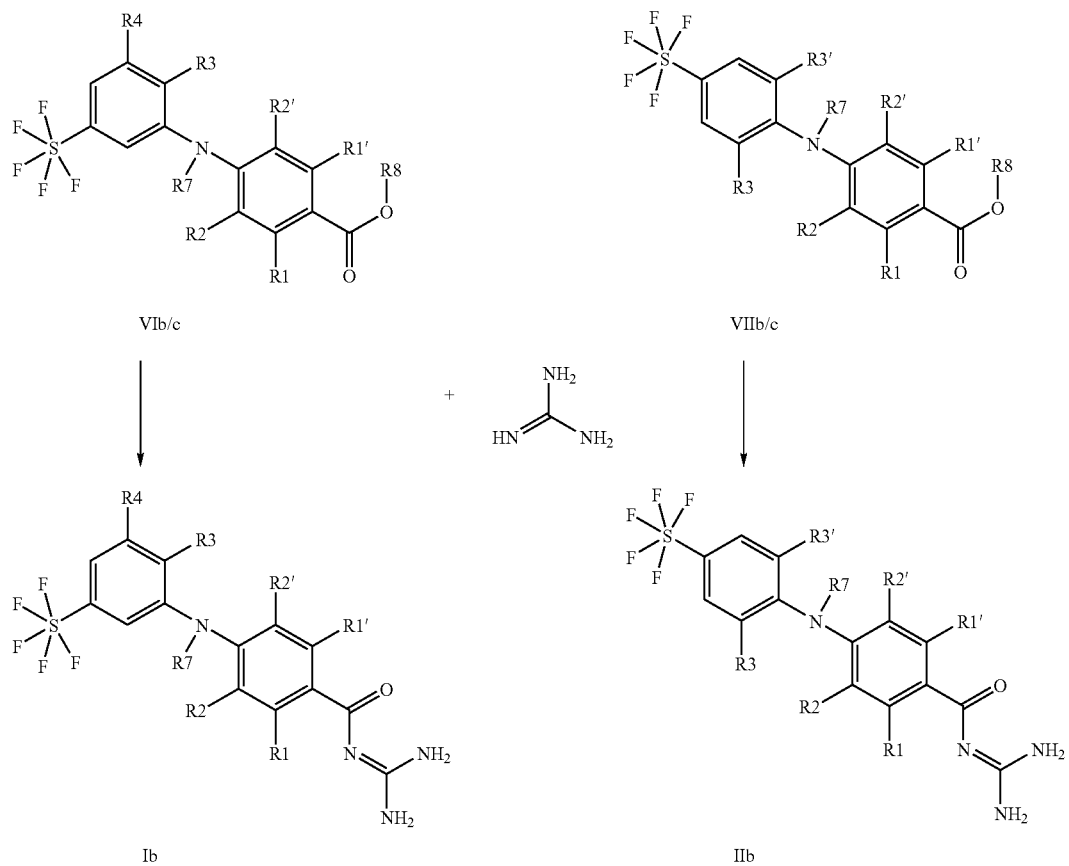

in which R1, R1', R2, R2', R3, R3', R4 and R7 have the meaning indicated above, and in which the meanings are
Hal F, Cl, Br or I
R8 hydrogen or alkyl having 1, 2, 3 or 4 carbon atoms.

The anilines of the formulae VIII or IX are sulfonated in a suitable solvent, preferably an inert solvent such as, for example, $CH_2Cl_2$, DMF or NMP with a sulfonyl chloride, for example methanesulfonyl chloride, in the presence of a base such as, for example, triethylamine, at a temperature between −30° C. and 100° C., preferably at a temperature between 0° C. and 60° C. This results either in the monosulfonated anilines of the formulae X or XI or the corresponding bis sulfonated anilines or a mixture of the two.

In the case of bis sulfonated anilines or of the mixture of the two, the elimination of a sulfonyl group is carried out by hydrolysis with a suitable nucleophile, preferably an aqueous alkali solution, such as, for example, aqueous NaOH solution, at a temperature between RT and 120° C.

The compounds of the formulae X and XI are deprotonated in a suitable solvent, preferably in a dipolar aprotic solvent such as, for example, acetonitrile, DMF, NMP or DMSO, with the aid of an inorganic base such as, for example, $K_2CO_3$ or $Cs_2CO_3$, or with the aid of an organic base such as, for example, triethylamine or TBTMG, at a temperature between 0° C. and the boiling point of the solvent used, and then reacted with an electrophilic aromatic compound of the formula V in a nucleophilic aromatic substitution at a temperature between 0° C. and the boiling point of the solvent used, preferably between RT and 160° C., to give the compounds of the formulae VIb or VIIb.

For the optional derivatization, the compounds of the general formulae VIb or VIIb are initially deprotonated with an inorganic base such as, for example, NaH, or an organic base such as, for example, TBTMG, at a temperature between −30° C. and 80° C., preferably at RT, and then reacted with a suitable electrophile such as, for example, methyl iodide or methanesulfonyl chloride, at a temperature between −30° C. and 80° C., preferably at RT, to give derivatives of the formulae VIc or VIIc.

The esters of the formulae VIb/c or VIIb/c can, such as, for example, for R7 is hydrogen, subsequently be hydrolyzed to give the carboxylic acids by dissolving them in a suitable solvent such as, for example, methanol or ethanol, and adding an aqueous alkali solution, for example aqueous NaOH solution. The reaction mixture is reacted at −30° C. to the boiling point of the the solvent, preferably at RT. The carboxylic acids are initially activated with one of the activation methods known to the skilled worker, preferably with CDI, in an inert solvent, preferably DMF or NMP, at a temperature between −30° C. and 100° C., preferably at RT, and subsequently reacted with guanidine, which has preferably been generated from guanidinium chloride and KOtBu in DMF or NMP, at a temperature between 0° C. and 100° C., preferably between RT and 80° C., to give the acylguanidines of the formulae Ib or IIb.

A further possibility is also to react the esters of the formulae VIb/c or VIIb/c directly as described in scheme 1 with either free guanidine base or, preferably, with guanidine chloride in the presence of a base to give the acylguanidines of the formula Ib or IIb.

The starting compounds of the formulae VIII, IX and V are commercially available or can be prepared by or in analogy to processes known to the skilled worker and described in the literature.

The present invention further relates to a process for preparing a compound of the formula I or II and/or the pharmaceutically acceptable salts thereof, in which X is $S(O)_{kk}$ (scheme 3), which comprises
a) reacting a thiophenol of the formulae XII or XIII with an aromatic compound of the formula V to give a compound of the formulae VIe or VIIe,
b) to prepare a compound of the formulae Ic or IIc in which kk is different from zero, oxidizing a compound of the formulae VIe or VIIe to a compound of formulae VIf or VIIf, and
c) reacting a compound of the formulae VIe/f or VIII/ef with guanidine to give an acylguanidine of the formulae Ic or IIc, Scheme 3

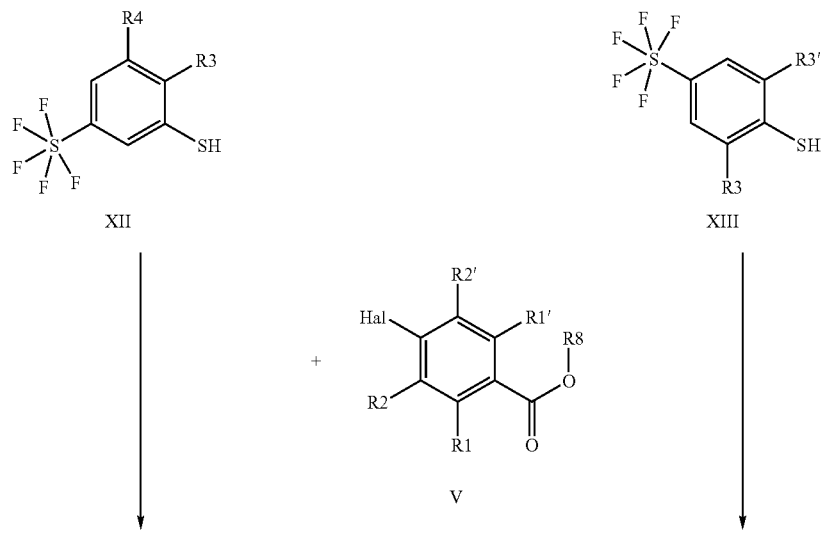

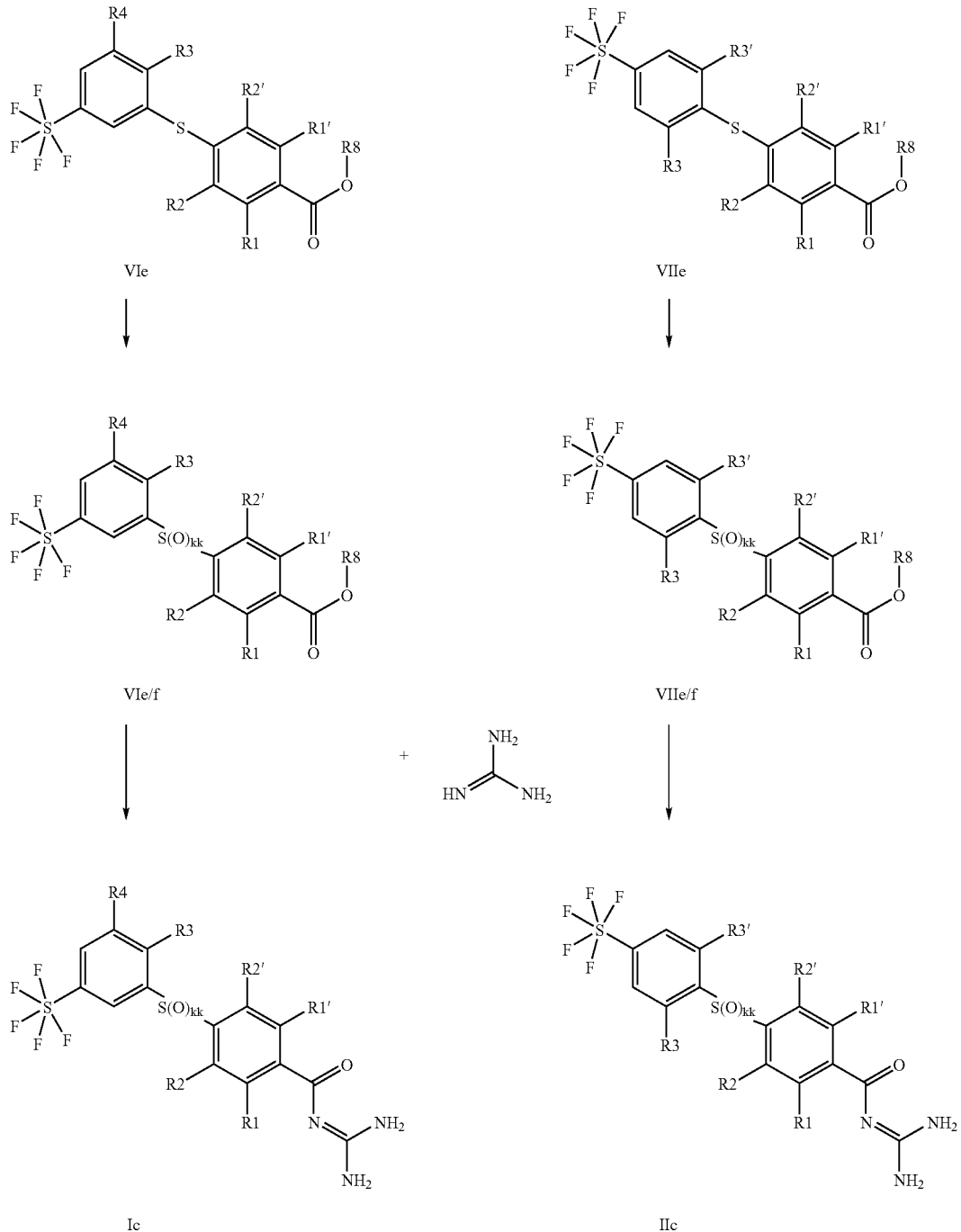

in which R1, R1', R2, R2', R3, R3', R4 and kk have the meaning indicated above, and in which the meanings are
Hal F, Cl, Br or I
R8 hydrogen or alkyl having 1, 2, 3 or 4 carbon atoms.

The thiophenols of the formulae XII or XIII are deprotonated in a suitable solvent, preferably in a dipolar aprotic solvent such as, for example, acetonitrile, DMF, NMP or DMSO, with the aid of an inorganic base such as, for example, $K_2CO_3$ or $Cs_2CO_3$ or with the aid of an organic base such as, for example, triethylamine or TBTMG, at a temperature between 0° C. and the boiling point of the solvent used, and then reacted with the electrophilic aromatic compound of the formula V in a nucleophilic aromatic substitution at a temperature between 0° C. and the boiling point of the solvent used, preferably between RT and 150° C., to give compounds of the formulae VIe or VIIe.

In the case where kk is zero, the esters of the formulae VIe or VIIe can subsequently be reacted with free guanidine base or guanidinium chloride in the presence of a base to give the acylguanidines of the formulae Ic or IIc as described above in scheme 1.

For the optional oxidation to compounds of the formula VIf or VIIf in which kk is 1 or 2, the thioethers of the formulae VIe or VIIe are dissolved in an inert solvent such as, for example, $CH_2Cl_2$, and reacted with a peroxide derivative, preferably with mCPBA, depending on the stoichiometry to give the sulfoxides or sulfones of the formulae VIf or VIIf at a temperature between −30° C. and the boiling point of the solvent, preferably at RT. The esters of the formulae VIf or VIIf obtained in this way are reacted as described in scheme 1 with free guanidine base or guanidinium chloride in the presence of a base to give the acylguanidines of the formulae Ic and IIc.

The esters of the formula VIe/f or VIIe/f in which R8 is alkyl can also be initially hydrolyzed to the carboxylic acids and subsequently reacted, preferably in the presence of an activating agent, with guanidine to give the acylguanidines of the formulae Ic or IIc.

The starting compounds of the formulae XII, XIII and V are commercially available or can be prepared by or in analogy to processes known to the skilled worker and described in the literature, for example the compounds of the formulae XII and XIII can be prepared in analogy to Rundel, Wolfgang; Chem. Ber. (1968), 101(8), 2956).

The invention further relates to a process for preparing a compound of the formula I or II and/or the pharmaceutically acceptable salts thereof in which X is a direct linkage (scheme 4), which comprises a) coupling a halide of the formula XIV or XV in a Suzuki coupling with a benzoic ester of the formula Va to give a biphenyl derivative of the formula VIg or VIIg, and b) reacting a compound of the formula VIg and VIIg with guanidine to give an acylguanidine of the formula Id or IId,

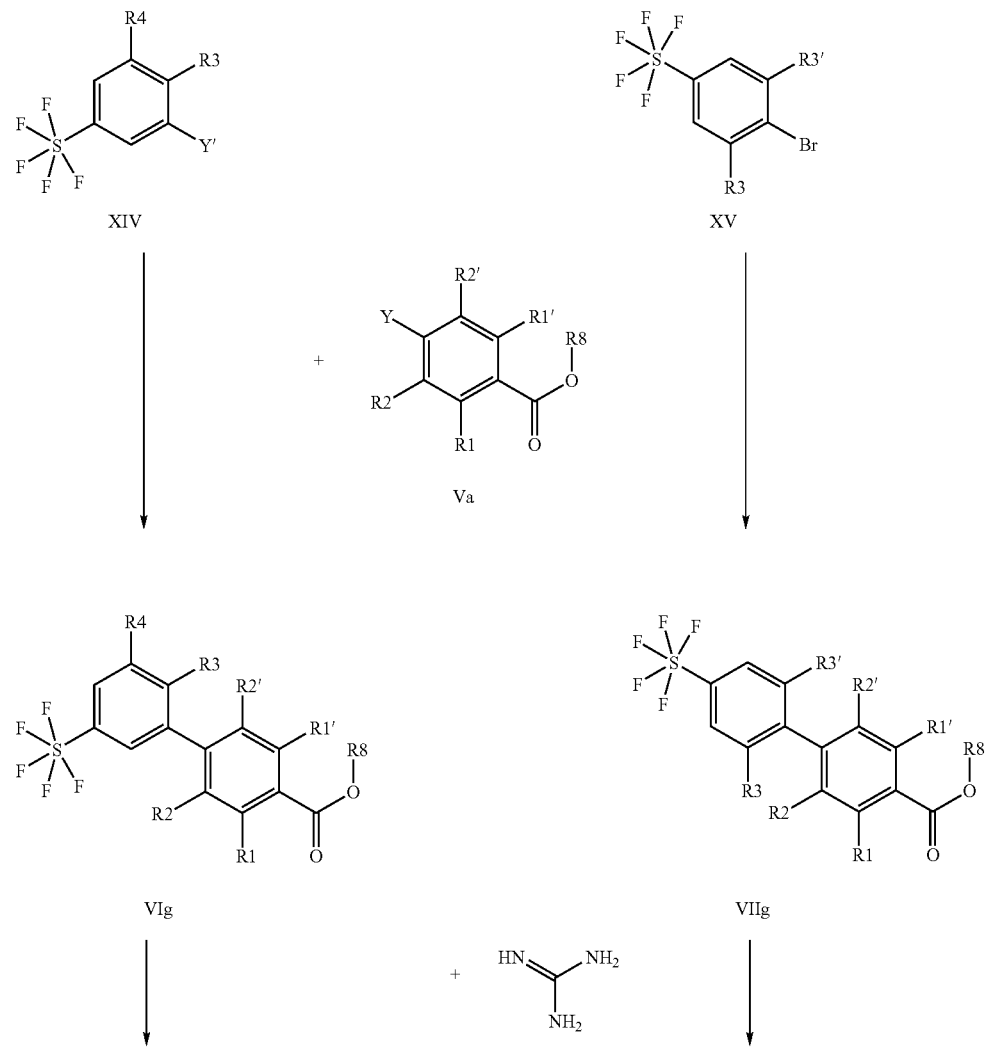

Scheme 4

-continued

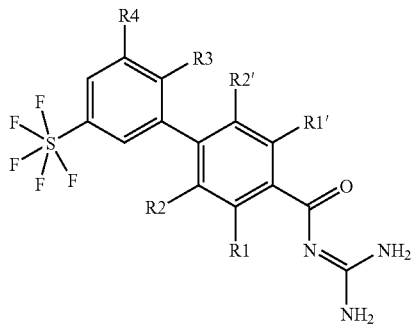

Id

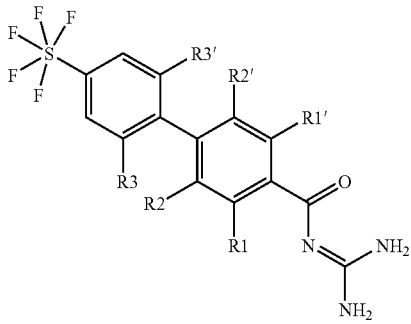

IId in which R1, R1', R2, R2', R3, R3' and R4 have the meaning indicated above, and in which the meanings are Y and Y' independently of one another Cl, Br or I R8 hydrogen or alkyl having 1, 2, 3 or 4 carbon atoms.

The pentafluorosulfanylaryl halides of the formulae XIV or XV are coupled in a Suzuki coupling with the benzoic ester of the formula Va. For this purpose, either the corresponding arylboronic acid is prepared from the halides of the formulae XIV or XV initially by processes known to the skilled worker. Or the arylboronic acid is prepared as intermediate in the reaction, for example with the aid of the compound of the formula XVI

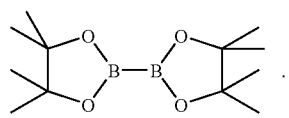

XVI

For this purpose, the pentafluorosulfanylaryl halide is stirred together with bis(pinacolato)diboron of the formula XVI and a base such as, for example, $K_2CO_3$ and a catalyst such as, for example, $Pd(dppf)_2$, in an suitable solvent, preferably DMF or NMP, at a temperature between RT and 120° C., preferably at 60° C.-100° C. This reaction mixture is then reacted with the ester of the formula Va at a temperature between RT and 120° C., preferably between 60° C. and 100° C., to give the biphenyl derivatives of the formulae VIg or VIIg. The esters of the general formula VIg and VIIg obtained in this way are reacted as described in scheme 1 to give the acylguanidines of the formulae Id or IId.

The starting compounds of the formulae XIV, XV, XVI and Va are commercially available or can be prepared by or in analogy to processes known to the skilled worker and described in the literature.

The working up and, if desired, the purification of the products and/or intermediates takes place by conventional methods such as extraction, chromatography or crystallization and conventional dryings.

The invention also includes precursors of the formulae VI and VII and the salts thereof

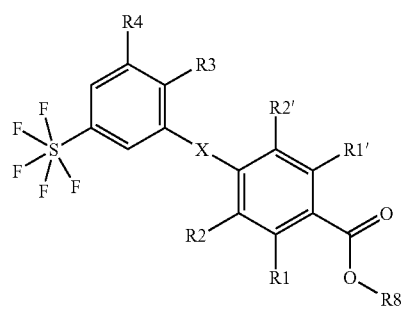

VI

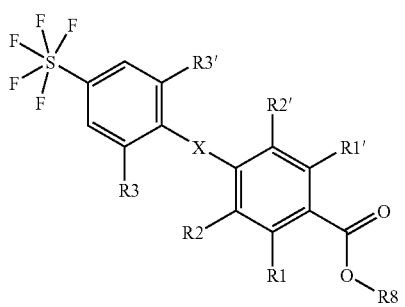

VII where R1, R1', R2, R2', R3, R3', R4 and X have the abovementioned meanings, and R8 is hydrogen or alkyl having 1, 2, 3 or 4 carbon atoms, and the use thereof as synthetic intermediates, for example for preparing active pharmaceutical ingredients such as, for example, compounds of the formula I or II and/or the pharmaceutically acceptable salts thereof.

Pentafluorosulfanylphenyl-substituted benzoylguanidines of the formulae I and II are generally weak bases and are able to bind acid to form salts. Suitable acid addition salts are in particular salts of all pharmacologically acceptable acids, for example halides, in particular hydrochlorides, lactates, sulfates, citrates, tartrates, acetates, phosphates, methylsulfonates, p-toluenesulfonates.

The compounds of the formulae I and II are substituted acylguanidines and inhibit the cellular sodium-proton antiporter ($Na^+/H^+$ exchanger, NHE), especially the NHE1 subtype.

Compared with known NHE inhibitors, the compounds of the invention are distinguished by an extremely high activity in the inhibition of Na⁺/H⁺ exchange, and by improved ADMET properties, for example by longer S9 stabilities (liver stabilities, stability to enzymatic attack) and longer half-lives in vivo. They moreover show good adsorption characteristics and a high bioavailability.

Because of the NHE-inhibitory properties, the compounds of the formula I and II and the pharmaceutically acceptable salts thereof are suitable for the prevention and treatment of diseases caused by activation or activated NHE, and of diseases caused secondarily by the NHE-related damage.

Since NHE inhibitors predominantly act via their effect on cellular pH regulation, they can generally be combined beneficially with other compounds which regulate the intracellular pH, with suitable combination partners being inhibitors of the carbonic anhydratase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine.

Thus, the NHE inhibitors of the invention are suitable for the treatment of diseases caused by ischemia and by reperfusion.

The compounds described herein are suitable because of their pharmacological properties as antiarrhythmic medicaments.

Owing to their cardioprotective component, the NHE inhibitors of the formula I and II and the pharmaceutically acceptable salts thereof are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias.

Because of their protective effects against pathological hypoxic and ischemic situations, the compounds of the formula I and II and the pharmaceutically acceptable salts thereof used according to the invention can, because of inhibition of the cellular Na⁺/H⁺ exchange mechanism, be used as medicaments for the treatment of all acute or chronic ischemia-induced damage or diseases induced primarily or secondarily thereby.

This also relates to their use as medicaments for surgical interventions. Thus, the compounds can be used during organ transplantations, it being possible to use the compounds both to protect the organs in the donor before and during the removal, to protect removed organs for example during treatment with or storage thereof in physiological bath liquids, and during transference to the recipient organism.

The compounds of the invention are likewise valuable medicaments with a protective effect when performing angioplastic surgical interventions, for example on the heart as well as on peripheral organs and vessels.

It has emerged that the compounds of the invention are exceptionally effective medicaments for life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of the formula I and II and the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of the formula I and II and the pharmaceutically acceptable salts thereof can be used when there is heart-damaging overproduction of thyroid hormones, thyrotoxicosis, or on external supply of thyroid hormones. The compounds of the formula I and II and the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, these being suitable for example for the treatment of stroke or of cerebral edema.

The compounds of the formula I and II and the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonic anhydratase inhibitors, for example with acetazolamide, and with other inhibitors of NHE or of the sodium-dependent chloride-bicarbonate exchanger (NCBE).

The compounds used according to the invention of the formula I and II and the pharmaceutically acceptable salts thereof are additionally likewise suitable for the treatment of types of shock such as, for example, of allergic, cardiogenic, hypovolemic and bacterial shock.

The compounds of the formula I and II and the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonic anhydratase such as, for example, with acetazolamide, is particularly beneficial.

The compounds of the formula I and II and the pharmaceutically acceptable salts thereof used according to the invention are additionally distinguished by a strong inhibitory effect on the proliferation of cells, for example fibroblast proliferation and the proliferation of smooth vascular muscle cells. The compounds of the formula I and II and the pharmaceutically acceptable salts thereof are therefore suitable as valuable therapeutic agents for diseases in which cellular proliferation represents a primary or secondary cause, and can therefore be used as antiatherosclerotics, agents for chronic renal failure, cancers.

It was possible to show that cell migration is inhibited by NHE inhibitors. The compounds of the formula I and II and the pharmaceutically acceptable salts thereof are therefore suitable as valuable therapeutic agents for dieases in which cell migration represents a primary or secondary cause, such as, for example, cancers with a pronounced tendency to metastasis.

The compounds of the formula I and II and the pharmaceutically acceptable salts thereof are further distinguished by a retardation or prevention of fibrotic disorders. They are thus suitable as excellent agents for the treatment of cardiac fibroses, and of pulmonary fibrosis, hepatic fibrosis, renal fibrosis and other fibrotic disorders. They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of the formula I and II and the pharmaceutically acceptable salts thereof are suitable for the prevention and treatment of high blood pressure and for the treatment of cardiovascular disorders. In these cases they can be used alone or with a suitable combination and formulation partner for the treatment of high blood pressure and of cardiovascular disorders. Thus, for example, one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone, can be combined. The NHE inhibitors of the present invention can further be used in combination with calcium channel blockers such as verapamil, diltiazem, amlodipine or nifedipine, and with ACE inhibitors such as, for example, ramipril, enalapril, lisinopril, fosinopril or captopril. Further beneficial combination partners are also beta-blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that NHE1 inhibitors have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs. NHE1 inhibitors can also be used to treat diseases caused by protozoa, malaria or coccidiosis in poultry.

It has additionally been found that NHE1 inhibitors show a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the compounds of the formula I and II and the pharmaceutically acceptable salts thereof lead to a marked reduction in the infarctions induced by metabolic abnormalities and, in particular, to a significant reduction in the induced infarct size and the severity thereof. Said compounds are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of the formula I and II and the pharmaceutically acceptable salts thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of the formula I and II and the pharmaceutically acceptable salts thereof, proves to be a favorable combination with enhanced effect and reduced use of active ingredients.

Thus, compounds of the formula I and II and the pharmaceutically acceptable salts thereof lead to effective protection against endothelial damage of various origins. This protection of the vessels against the syndrome of endothelial dysfunction means that the compounds of the formula I and II and the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that benzoylguanidines of the formula I and II and the pharmaceutically acceptable salts thereof are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute antidiabetic effects, the compounds of the formula I and II and the pharmaceutically acceptable salts thereof counteract the development of late complications of diabetes and can therefore be used as medicaments for the prevention and treatment of late damage from diabetes, such as diabetic nephropathy, diabetic neuropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

The NHE inhibitors of the invention of the formula I and II and the pharmaceutically acceptable salts thereof show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. The compounds of the formula I and II and the pharmaceutically acceptable salts thereof are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart which is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of the formula I and II and the pharmaceutically acceptable salts thereof are thus outstandingly suitable for the treatment and prevention of heart failure, of congestive heart failure (CHF).

Whereas the treatment of various forms of cancer which have already occurred is already known, it was now extremely surprising that not only is it possible to cure a cancer which has already occurred through inhibition of proliferation, but there is also prevention and highly significant retardation of the age-related incidence of cancer through NHE inhibitors. A particularly noteworthy finding is that the disorders, occurring as a result of aging, of all organs and not only certain types of cancer are suppressed or occur with a highly significant delay. The compounds of the formula I and II and the pharmaceutically acceptable salts thereof are thus outstandingly suitable for the treatment and, in particular, the prevention of age-related types of cancer.

With NHE1 inhibitors there is now found to be not only a delay, shifted highly significantly in time and beyond the normal statistical extent, in the occurrence of age-related disorders of all the organs investigated, including the heart, vessels, liver etc., but also a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhibitors, angiotensin receptor antagonists, diuretics, $Ca^{2+}$ channel blockers etc. or with metabolism-normalizing medicaments such as cholesterol-lowering agents.

The compounds of the formula I and II and the pharmaceutically acceptable salts thereof are thus outstandingly suitable for the prevention of age-related tissue changes and for prolonging life while retaining a high quality of life. The compounds of the invention are effective inhibitors of the cellular sodium-proton antiporter (Na/H exchanger) which in a large number of disorders (essential hypertension, atherosclerosis, diabetes etc.) is also increased in cells which are readily amenable to measurements, such as, for example, in erythrocytes, platelets or leucocytes. The compounds used according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

Also claimed is a medicine for human, veterinary or phytoprotective use, comprising an effective amount of a compound of the formula I and II and the pharmaceutically acceptable salts thereof, together with pharmaceutically acceptable carriers and additives, alone or in combination with other pharmacological active ingredients or medicaments.

Medicaments which comprise a compound of the formula I and II and the pharmaceutically acceptable salts thereof can in this connection be administered, for example, orally, parenterally, intravenously, rectally, percutaneously or by inhalation, the preferred administration being dependent on the particular characteristics of the disorder. The compounds I and II may moreover be used alone or together with pharmaceutical excipients, both in veterinary medicine and in human medicine. The medicaments generally comprise active ingredients of the formula I and II and the pharmaceutically acceptable salts thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and II and the pharmaceutically acceptable salts thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I and II to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or II and/or the pharmaceutically acceptable salts thereof for a patient weighing about 75 kg is at least 0.001 mg/kg, preferably 0.01 mg/kg, to a maximum of 10 mg/kg, preferably 1 mg/kg, of body weight. For acute episodes of the disorder, for example immediately after suffering a myocardial infarction, higher dosages may also be necessary, e.g. up to 4 single doses a day. Up to 800 mg a day may be necessary, in particular on i.v. administration, for example for a patient with infarction in the intensive care unit. The daily dose can be divided into a plurality of, for example up to 4, single doses.

List of Abbreviations:
ADMET adsorption—distribution—metabolism—excretion—toxicology
Bis(pinacolato)diboron 4,4,4',4',5,5,5',5'-octamethyl-2,2'-bi-1,3,2-dioxaborolane
CDI diimidazol-1-ylmethanone
DIP diisopropyl ether
DIPEA diisopropylethylamine
DME 1,2-dimethoxyethane
DMF N,N-dimethylformamide
DMSO dimethyl sulfoxide
EA ethyl acetate (EtOAc)
eq. equivalent
HEP n-heptane
HOAc acetic acid
KOtBu potassium 2-methylpropan-2-olate
MeOH methanol
mp melting point
mCPBA 3-chloroperbenzoic acid
MTB tert-butyl methyl ether
NMP 1-methylpyrrolin-2-one
Pd(dppf)2 [1,1'-bis(diphenylphosphino)ferrocene]palladium (II) chloride-methylene chloride complex (1:1)
RT room temperature
TBTMG N"-tert-butyl-N,N,N',N'-tetramethylguanidine
THF tetrahydrofuran
TMEDA N,N,N'N'-tetramethylethane-1,2-diamine

EXAMPLE 1

N-[5-Methanesulfonyl-2-methyl-4-(3-pentafluorosulfanylphenoxy)-benzoyl]guanidine

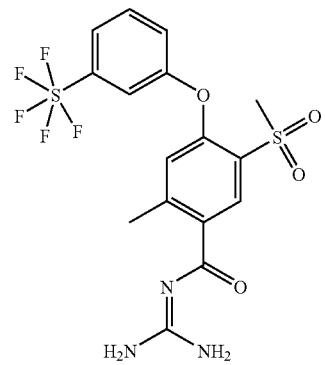

29 a) 3-Pentafluorosulfanylphenol

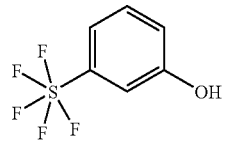

5.0 g of 3-pentafluorosulfanylaniline were suspended in 50 ml of a 35% aqueous H$_2$SO$_4$ solution. Then, at 0° C., a solution of 1.57 g of NaNO$_2$ in 5 ml of water was added dropwise over the course of 10 minutes. The mixture was stirred at 0° C. for 40 minutes. Then a solution, cooled to 0° C., of 8.56 g of Cu(NO$_3$)2 in 50 ml of water was added to this suspension. Immediately thereafter, 3.26 g of Cu$_2$O was also added, whereupon marked evolution of gas was observable. 3 extractions each with 100 ml of CH$_2$Cl$_2$ were carried out, the org. phase was washed with 100 ml of a saturated aqueous NaCl solution and dried over MgSO$_4$, and the solvent was removed in vacuo. Chromatography with DIP on a short silica gel column afforded 3.5 g of the phenol as colorless oil.

R$_f$ (EA/HEP 1:10)=0.15 MS (El): 220 b) Methyl 5-methanesulfonyl-2-methyl-4-(3-pentafluorosulfanylphenoxy)benzoate

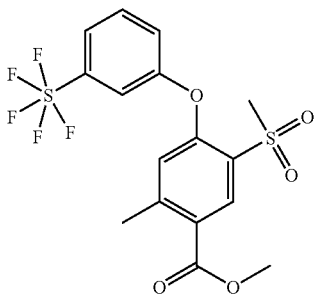

600 mg of methyl 4-fluoro-5-methanesulfonyl-2-methylbenzoate, 700 mg of 3-pentafluorosulfanylphenol and 1.6 g of Cs$_2$CO$_3$ were stirred in 4 ml of anhydrous DMF at 100° C. for 3 h. The mixture was then cooled to RT, diluted with 100 ml of EA and washed 3 times with 20 ml of water each time. The residue after drying over MgSO$_4$ and removal of the solvent in vacuo was chromatographed on silica gel with DIP. 300 mg of a colorless oil were obtained.

R$_f$ (DIP)=0.27 MS (ES$^{30}$): 446 c) N-[5-Methanesulfonyl-2-methyl-4-(3-pentafluorosulfanylphenoxy)benzoyl]-guanidine 385 mg of guanidinium chloride were stirred together with 377 mg of KOtBu in 10 ml of anhydrous DMF at RT for 30 minutes. This suspension was then added to a solution of 300 mg of methyl 5-methanesulfonyl-2-methyl-4-(3-pentafluorosulfanylphenoxy)benzoate in 5 ml of anhydrous DMF and left to stand and at RT for 5 h. The mixture was diluted with 30 ml of EA, washed 3 times with 5 ml of water each time and dried over MgSO$_4$, and the solvent was removed in vacuo, and the residue was chromatographed on silica gel with EA/MeOH 10:1.200 mg of a colorless amorphous solid were obtained. Recrystallization from DIP/MTB 3:1 afforded colorless crystals with mp=166-168° C.

R$_f$ (EA/MeOH 10:1)=0.26 MS (ES$^+$): 473

30

EXAMPLE 2

N-[5-Methanesulfonyl-2-methyl-4-(4-pentafluorosulfanylphenoxy)-benzoyl]guanidine

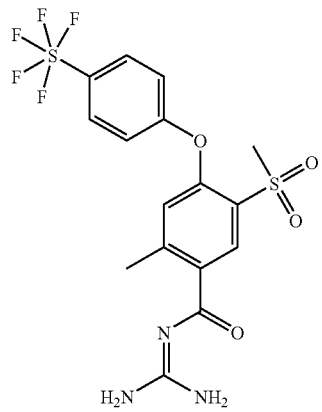

The title compound of example 2 was synthesized in analogy to example 1.

R$_f$ (EA/MeOH 10:1)=0.26 MS (ES$^+$): 473

EXAMPLE 3

N-[5-Methanesulfonyl-2-methyl-4-(4-pentafluorosulfanylphenylsulfanyl)benzoyl]-guanidine,

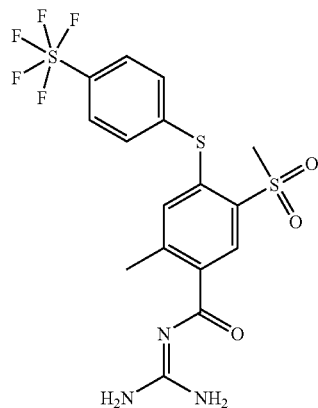

a) 4-Pentafluorosulfanylthiophenol

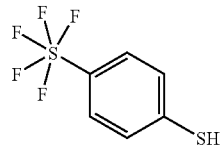

3.0 g of 4-pentafluorosulfanylaniline were dissolved in 10 ml of acetic acid and added to 30 ml of a 35% aqueous H$_2$SO$_4$ solution. Then, at 0° C., a solution of 1.0 g of NaNO$_2$ in 8 ml of water was added, and the mixture was stirred at 0° C. for 10 minutes. The solution of the diazonium salt obtained in this way was added slowly to a solution of Na₂S₂ (prepared by dissolving 0.61 g of sulfur with 4.4 g of Na₂S and 1.0 g of NaOH in 30 ml of water) at 50-60° C. The mixture was stirred at 60° C. for 30 minutes. Cooling was followed by extraction with 300 ml of diethyl ether and then washing with 100 ml of a 10% aqueous HCl solution. The residue after drying over MgSO₄ and removal of the solvent in vacuo was taken up in 100 ml of anhydrous diethyl ether. 0.52 g of LiAlH₄ was added in portions to this solution at 0° C. and then stirred at RT for 1 h. The reaction mixture was then cautiously added to 100 ml of a 10% aqueous HCl solution, and the ethereal phase was washed with 100 ml of a saturated aqueous NaCl solution. The residue after drying over MgSO₄ and removal of the solvent in vacuo was chromatographed on silica gel with HEP/DIP 1:1. 280 mg of a colorless oil were obtained.

$R_f$(DIP)HEP 1:1)=0.73 b) Methyl 5-methanesulfonyl-2-methyl-4-(4-pentafluorosul-fanylphenyl-sulfanyl)benzoate

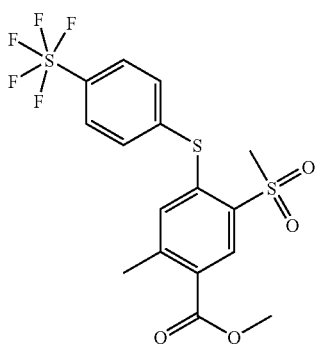

0.28 g of 4-pentafluorosulfanylthiophenol, 0.36 g of methyl 4-bromo-5-methanesulfonyl-2-methylbenzoate and 0.33 g of K₂CO₃ were dissolved in 8 ml of anhydrous DMF and stirred at 110° C. for 2 h. The reaction mixture was then poured into 100 ml of water and extracted twice with 100 ml of EA each time. The EA phase was then washed twice with 30 ml of water each time. The residue after drying over MgSO₄ and removal of the solvent in vacuo was chromatographed on silica gel with CH₂Cl₂/DIP 1:2. 320 mg of a colorless foam were obtained.

$R_f$(CH₂Cl₂DIP 1:2)=0.85 c) N-[5-Methanesulfonyl-2-methyl-4-(4-pentafluorosulfa-nylphenylsulfanyl)-benzoyl]guanidine 41 mg of KOtBu and 42 mg of guanidinium chloride were stirred in 1 ml of anhydrous DMF at RT for 30 minutes. Then a solution of 34 mg of methyl 5-methanesulfonyl-2-methyl-4-(4-pentafluorosulfanylphenylsulfanyl)benzoate in 1 ml of anhydrous DMF was added. The mixture was stirred at RT for 5 h and then diluted with 10 ml of water, the pH was adjusted to 8 with aqueous HCl solution, and the product was filtered off with suction. Drying in vacuo at RT resulted in 35 mg of an amorphous solid.

$R_f$(EA)=0.16 MS (ES⁺): 490

EXAMPLE 4

N-[5-Methanesulfonyl-2-methyl-4-(4-pentafluoro-sulfanylphenylsulfonyl)-benzoyl]guanidine

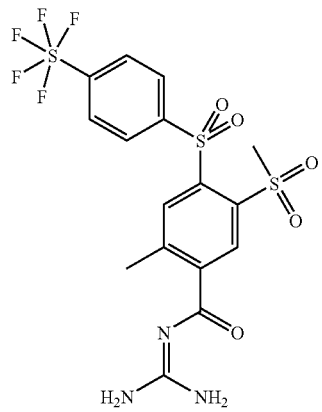

a) Methyl 5-methanesulfonyl-2-methyl-4-(4-pentafluorosul-fanylphenyl-sulfonyl)benzoate

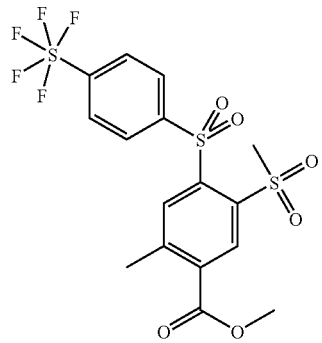

100 mg of methyl 5-methanesulfonyl-2-methyl-4-(4-pentafluorosulfanylphenyl-sulfanyl)benzoate (example 3b) were dissolved in 5 ml of CH₂Cl₂ and, at RT, 136 mg of mCPBA were added. After stirring at RT for 20 h, a further 50 mg of mCPBA were added, and the mixture was stirred at RT for 1 h. It was diluted with 100 ml of CH₂Cl₂ and then washed firstly twice with 10 ml of a saturated aqueous Na₂SO₃ solution each time and then twice with 10 ml of a saturated aqueous Na₂CO₃ solution each time. The solution was dried over MgSO₄ and the solvent was removed in vacuo. 100 mg of a colorless foam were obtained.

$R_f$(CH₂Cl₂)=0.29 b) N=[5-Methanesulfonyl-2-methyl-4-(4-pentafluorosulfa-nylphenylsulfonyl)-benzoyl)guanidine 114 mg of KOtBu and 116 mg of guanidinium chloride were stirred in 5 ml of anhydrous DMF at RT for 30 minutes. Then a solution of 100 mg of methyl 5-methanesulfonyl-2-methyl-4-(4-pentafluorosulfanylphenylsulfonyl)benzoate in 5 ml of anhydrous DMF was added. The mixture was stirred at RT for 15 h and then diluted with 15 ml of water, the pH was adjusted to 8 with aqueous HCl solution, and the product was filtered off with suction. Drying in vacuo at RT resulted in 30 mg of an amorphous solid.

$R_f$(EA)=0.14 MS (ES⁺): 1043 (2M+H)⁺

EXAMPLE 5

N-[5-Methanesulfonyl-2-methyl-4-(3-pentafluoro-sulfanylphenylamino)-benzoyl]guanidine,

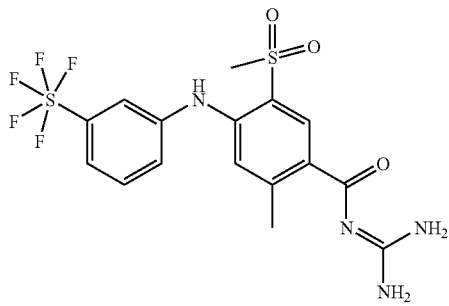

a) N-Methanesulfonyl-(3-pentafluorosulfanylphenyl)methanesulfonamide

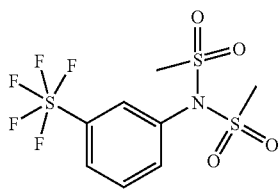

1.5 g of 3-pentafluorosulfanylaniline were dissolved in 100 ml of $CH_2Cl_2$, and 2.8 ml of triethylamine were added. Then 1.6 ml of methanesulfonyl chloride were slowly added dropwise at RT. After standing at RT for 2 days, the volatile constituents were removed in vacuo. The residue was taken up in 200 ml of EA and washed 3 times with 50 ml of a 10% aqueous $NaHSO_4$ solution each time. The solution was dried over $MgSO_4$ and the solvent was removed in vacuo. 2.3 g of a colorless oil were obtained.

MS (EI): 375 b) N-(3-Pentafluorosulfanylphenyl)methanesulfonamide

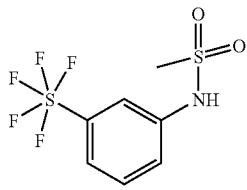

2.3 g of N-methanesulfonyl-(3-pentafluorosulfanylphenyl)methanesulfonamide were dissolved in 30 ml of MeOH, 8 ml of a 2N aqueous NaOH solution were added, and the mixture was heated under reflux for 3 h. After cooling, the volatile constituents were removed in vacuo, and the residue was then taken up in 200 ml of water and insoluble constituents were filtered off. The filtrate was then adjusted to pH=1 with an aqueous HCl solution and stirred for 2 h, and the product was filtered off with suction. 1.2 g of a yellowish solid were obtained; mp=80-82° C.

MS (EI): 297 c) Methyl 5-methanesulfonyl-2-methyl-4-(3-pentafluorosulfanylphenyl-amino)benzoate

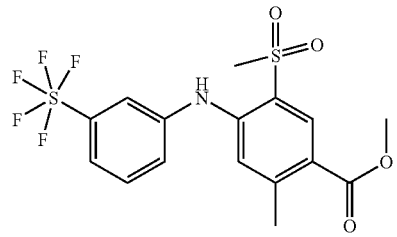

1.0 g of N-(3-pentafluorosulfanylphenyl)methanesulfonamide, 0.8 g of methyl 4-fluoro-5-methanesulfonyl-2-methylbenzoate and 1.4 ml of TBTMG were dissolved in 10 ml of NMP (anhydrous) and stirred at 150° C. for 7 h. The mixture was then diluted with 100 ml of EA and washed firstly 3 times with 30 ml of a saturated aqueous $Na_2CO_3$ solution each time and then 3 times with 30 ml of a saturated aqueous $NaHSO_4$ solution each time. The residue after drying over $MgSO_4$ and removal of the solvent in vacuo was chromatographed on silica gel with DIP. 370 mg of a resinous solid were obtained.

$R_f$ (DIP)=0.29 MS (E): 445 d) 5-Methanesulfonyl-2-methyl-4-(3-pentafluorosulfanylphenylamino)benzoic acid

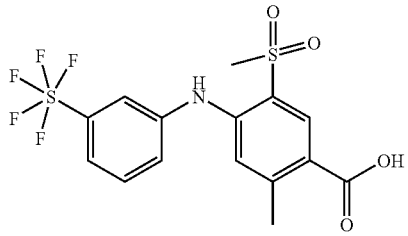

470 mg of KOtBu and 480 mg of guanidinium chloride were stirred in 5 ml of DMF (anhydrous) at RT for 1 h. This suspension was then added to 370 mg of methyl 5-methanesulfonyl-2-methyl-4-(3-pentafluorosulfanylphenylamino)benzoate and stirred at RT for 3 h. The mixture was then stirred at 70° C. for 2 h. Reaction (to give the acylguanidine) was negligible and thus the ester was hydrolyzed by adding 1 ml of a 2N aqueous NaOH solution and 5 ml of MeOH and stirring at RT for 6 h. The volatile constituents were then removed in vacuo, the residue was taken up in 30 ml of water, and the pH was adjusted to 2 with aqueous HCl solution. The product precipitates as a white amorphous solid which liquefies again on the filter and is therefore redissolved in 30 ml of EA. The solvent is removed in vacuo to result in 230 mg of a white foam.

$R_f$ (EA)=0.47 MS (ES⁻): 430 e) N-[5-Methanesulfonyl-2-methyl-4-(3-pentafluorosulfanylphenylamino)-benzoyl]guanidine 220 mg of 5-methanesulfonyl-2-methyl-4-(3-pentafluorosulfanylphenylamino)benzoic acid were dissolved in 2 ml of DMF (anhydrous), and 108 mg of CDI were added. The mixture was then stirred at RT for 6 h. At the same time, 290 mg of guanidinium chloride and 290 mg of KOtBu were dissolved in 2 ml of DMF (anhydrous) and stirred at RT for 30 minutes. This guanidine suspension was then added to the activated acid derivative imidazol-1-yl-[5-methanesulfonyl-2-methyl-4-(3-pentafluorosulfanylphenylamino)phenyl]methanone and left to stand at RT for 20 h.

The reaction mixture was then poured into 50 ml of water, adjusted to pH=8 with an aqueous HCl solution and extracted 3 times with 30 ml of EA each time. The residue after drying over MgSO$_4$ and removal of the solvent in vacuo was chromatographed on silica gel with EA/MeOH 10:1. 170 mg of a colorless foam were obtained.

R$_f$ (EA/MeOH 10:1)=0.13 MS (ES$^+$): 473

EXAMPLE 6

N-[5-Methanesulfonyl-2-methyl-4-(4-pentafluorosulfanylphenyl-amino)benzoyl]guanidine

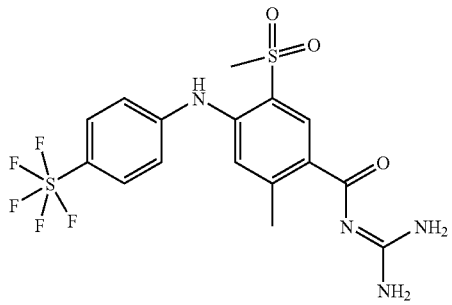

a) Methyl 5-methanesulfonyl-2-methyl-4-(4-pentafluorosulfanylphenyl-amino)benzoate

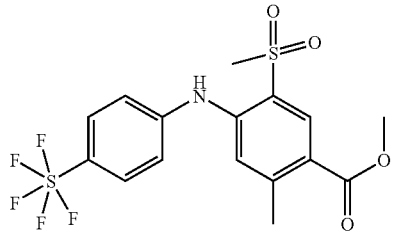

The starting material was synthesized in analogy to example 5a)-c).

b) 5-Methanesulfonyl-2-methyl-4-(4-pentafluorosulfanylphenylamino)benzoic acid

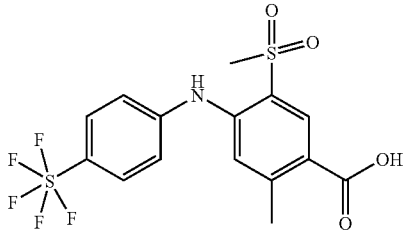

70 mg of methyl 5-methanesulfonyl-2-methyl-4-(4-pentafluorosulfanyl-phenylamino)benzoate were dissolved in 2 ml of MeOH, and 0.12 ml of a 2N aqueous NaOH solution was added. The mixture was stirred at RT for 2 h and then left to stand at RT for 16 h. The reaction mixture was then poured into 50 ml of water, adjusted to pH=2 with aqueous HCl solution and stirred at RT for 30 minutes, and finally the product was filtered off with suction. 66 mg of colorless crystals were obtained, mp 106-109° C.

MS (ES$^-$): 430 c) N-[5-Methanesulfonyl-2-methyl-4-(4-pentafluorosulfanylphenylamino)-benzoyl]guanidine 65 mg of 5-methanesulfonyl-2-methyl-4-(4-pentafluorosulfanylphenylamino)benzoic acid were dissolved in 3 ml of DMF (anhydrous), 37 mg of CDI were added, and the mixture was left to stand at RT for 4 h. At the same time, 87 mg of guanidinium chloride and 85 mg of KOtBu were stirred in 3 ml of DMF at RT for 30 minutes. This suspension was then added to the solution of the activated acid derivative imidazol-1-yl-[5-methanesulfonyl-2-methyl-4-(3-pentafluorosulfanylphenylamino)-phenyl]methanone and stirred at RT for 2 h. The reaction mixture was then poured into 80 ml of water, adjusted to pH=8 with aqueous HCl solution and extracted twice with 20 ml of EA each time. The residue after drying over MgSO$_4$ and removal of the solvent in vacuo was chromatographed on silica gel with EA/MeOH 10:1. 32 mg of a colorless foam was obtained.

R$_f$ (EA/MeOH 10:1)=0.31 MS (ES$^+$): 473

EXAMPLE 7

N-{5-Methanesulfonyl-2-methyl-4-[methyl-(3-pentafluorosulfanylphenyl)-amino]benzoyl}guanidine

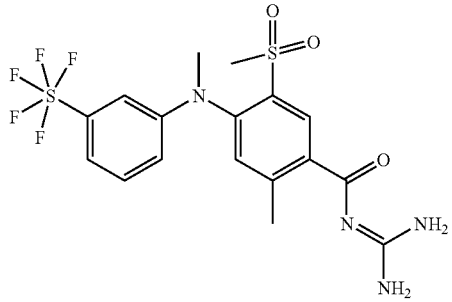

a) Methyl 5-methanesulfonyl-2-methyl-4-[methyl-(3-pentafluorosulfanylphenyl)-amino]benzoate

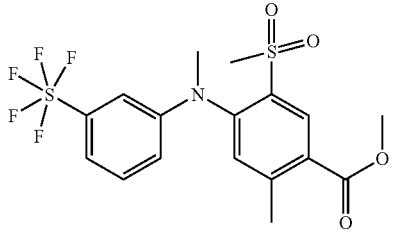

150 mg of methyl 5-methanesulfonyl-2-methyl-4-(3-pentafluorosulfanyl-phenylamino)benzoate (example 5 c) were dissolved in 2 ml of DMF (anhydrous), 13.5 mg of NaH were added, and the mixture was stirred at RT for 15 minutes. Then 15 μl of CH$_3$I were injected and the mixture was left to stand at RT for 18 h. The reaction mixture was then poured into 10 ml of a saturated aqueous NaHCO$_3$ solution and extracted with 40 ml of EA. The organic phase was subsequently washed with 10 ml of water. Drying over MgSO₄ and removal of the solvent in vacuo resulted in 120 mg of a pale yellow foam.

R$_f$ (DIP)=0.24 MS (ES⁺): 460 b) N-{5-Methanesulfonyl-2-methyl-4-[methyl-(3-pentafluorosulfanylphenyl)-amino]benzoyl}guanidine 146 mg of KOtBu and 150 mg of guanidinium chloride were stirred in 3 ml of DMF (anhydrous) at RT for 30 minutes. Then 120 mg of methyl 5-methanesulfonyl-2-methyl-4-[methyl-(3-pentafluorosulfanylphenyl)amino] benzoate were added, stirred at RT for 2 h and left to stand at RT for 15 h. The reaction mixture was then poured into 50 ml of water and adjusted to pH=8 with aqueous HCl solution. Stirring at RT for 30 minutes was followed by extraction twice with 20 ml of EA each time, and then the organic phase was washed twice with 5 ml of water each time. Drying over MgSO₄ and removal of the solvent in vacuo resulted in 53 mg of a pale yellow foam.

R$_f$ (EA/MeOH 10:1)=0.17 MS (ES⁺): 973 (2M+H)⁺

EXAMPLE 8

N-{5-Methanesulfonyl-2-methyl-4-[methyl-(4-pentafluorosulfanyl-phenyl)amino]benzoyl}guanidine

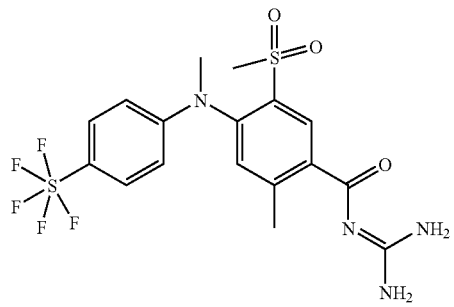

The title compound of example 8 was synthesized from example 6a) in analogy to example 7:

R$_f$ (EA/MeOH 10:1)=0.26 MS (ES⁺): 973 (2M+H)⁺

EXAMPLE 9

N-(2-Methanesulfonyl-5-methyl-4'-pentafluorosulfanylbiphenyl-4-carbonyl)guanidine

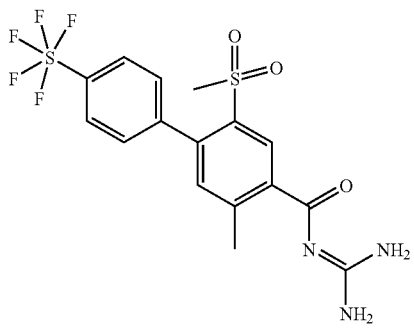

a) 1-Bromo-4-pentafluorosulfanylbenzene

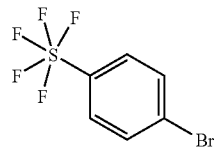

5.0 g of 4-pentafluorosulfanylaniline were dissolved in 20 ml of acetic acid and, at 0° C., a saturated aqueous HBr solution was added. Then at 0° C., a solution of 1.9 of NaNO₂ in 5 ml of water was slowly added dropwise over the course of 5 minutes. The reaction mixture was stirred at 0° C. for 10 minutes and then added in portions to a suspension of 6.5 g of CuBr in 20 ml of a half-saturated aqueous HBr solution at 0° C. Nitrogen is liberated during this. The mixture was stirred at 0° C. for 30 minutes and then at RT for 1 h. It was subsequently extracted 3 times with 100 ml of HEP each time, and then the HEP was washed twice with 50 ml of a saturated aqueous Na₂CO₃ solution each time. The residue after drying over MgSO₄ and removal of the solvent in vacuo was chromatographed on silica gel with HEP. 1.8 g of a colorless oil were obtained.

R$_f$ (HEP)=0.50 MS (El): 284 b) Methyl 2-methanesulfonyl-5-methyl-4'-pentafluorosulfanylbiphenyl-4-carboxylate

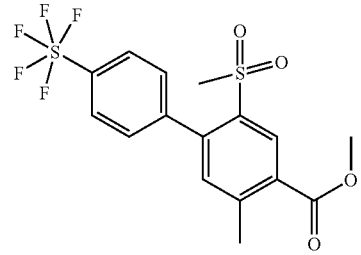

150 mg of 1-bromo-4-pentafluorosulfanylbenzene were stirred together with 135 mg of bis(pinacolato)diboron, 156 mg of potassium acetate and 64 mg of Pd(dppf)2 in 4 ml of DMF at 80° C. for 2 h. Then 163 mg of methyl 4-bromo-5-methanesulfonyl-2-methylbenzoate, 337 mg of Na₂CO₃, 64 mg of Pd(dppf)2 and 2 ml of water were added, and stirring was continued at 80° C. for 3 h. Cooling was followed by dilution with 50 ml of EA and washing twice with 10 ml of water each time. The residue after drying over MgSO₄ and removal of the solvent in vacuo was chromatographed on silica gel with DIP. 150 mg of a colorless oil were obtained.

R$_f$ (DIP)=0.28 MS (Cl): 430 c) N-(2-Methanesulfonyl-5-methyl-4'-pentafluorosulfanylbiphenyl-4-carbonyl)-guanidine 186 mg of guanidinium chloride and 182 mg of KOtBu were stirred in 5 ml of DMF (anhydrous) at RT for 30 minutes. This suspension was then added to 140 mg of methyl 2-methanesulfonyl-5-methyl-4'-pentafluorosulfanylbiphenyl-4-carboxylate and stirred at RT for 4 h. This was followed by pouring into 20 ml of water and adjustment of the pH to 8 with aqueous HCl solution. The product subsequently precipitates and is filtered off with suction. 100 mg of white crystals are obtained, mp 238-240° C.

R$_f$ (EA/MeOH 10:1)=0.32 MS (ES⁺): 458

EXAMPLE 10

N-(2-Methanesulfonyl-5-methyl-3'-pentafluorosulfanylbiphenyl-4-carbonyl)guanidine

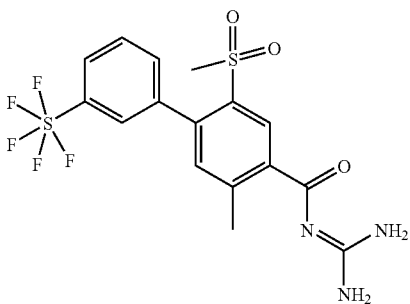

The title compound of example 10 was synthesized in analogy to example 9.

mp 169-175° C.

$R_f$ (EA/MeOH 10:1)=0.32 MS (ES$^+$): 458

EXAMPLE 11

N-(2-Methanesulfonyl-5,2'-dimethyl-4'-pentafluorosulfanylbiphenyl-4-carbonyl)guanidine

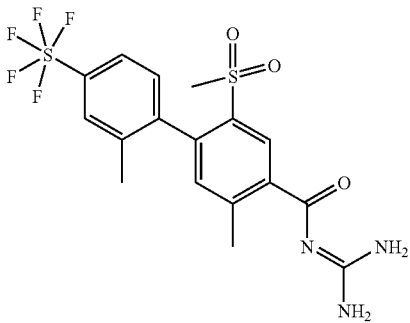

The title compound of example II was synthesized in analogy to example 9.

MS (ES$^+$): 943 (2M+H)$^+$

NHE Inhibition Method

The NHE-1 inhibition IC$_{50}$ was determined in an FLIPR assay by measurement of the recovery in pH$_i$ in transfected cell lines which express human NHE-1.

The assay was carried out in an FLIPR (fluorescent imaging plate reader) with black-walled 96-well microtiter plates with clear bases. The transfected cell lines expressing the various NHE subtypes (the parental cell line LAP-1 shows no endogenous NHE activity as a result of mutagenesis and subsequent selection) were seeded the preceding day at a density of ~25 000 cells/well.

The growth medium for the transfected cells (Iscove+10% fetal calf serum) additionally contained G418 as selection antibiotic in order to ensure the presence of the transfected sequences.

The actual assay started with the removal of the growth medium and addition of 100 µl of loading buffer per well (5 µM BCECF-AM [2',7'-bis(carboxyethyl)-5- (and -6-)carboxyfluorescein, acetoxymethyl ester] in 20 mM NH$_4$Cl, 115 mM choline chloride, 1 mM MgCl$_2$, 1 mM CaCl$_2$, 5 mM KCI, 20 mM HEPES, 5 mM glucose; pH 7.4 [adjusted with KOH]). The cells were then incubated at 37° C. for 20 minutes. This incubation led to loading of the cells with the fluorescent dye whose fluorescence intensity depends on pHi, and with NH$_4$Cl which makes the cells slightly alkaline. The nonfluorescent dye precursor BCECF-AM is, as ester, membrane-permeable. The actual dye BCECF is not membrane-permeable but is liberated inside cells by esterases.

After this incubation for 20 minutes, the loading buffer which contained NH$_4$Cl and free BCECF-AM was removed by washing three times in a cell washer (Tecan Columbus) with in each case 400 µl of washing buffer (133.8 mM choline chloride, 4.7 mM KCI, 1.25 mM MgCl$_2$, 1.25 mM CaCl$_2$, 0.97 mM K$_2$HPO$_4$, 0.23 mM KH$_2$PO$_4$, 5 mM HEPES, 5 mM glucose; pH 7.4 [adjusted with KOH]). The residual volume remaining in the wells was 90 µl (50-125 µl possible). This washing step removed the free BCECF-AM and resulted, as a consequence of the removal of the external NH$_4^+$ ions, in intracellular acidification (~pH$_i$ 6.3-6.4).

Since the equilibrium of intracellular NH$_4^+$ with NH$_3$ and H$^+$ was disturbed by the removal of the extracellular NH$_4^+$ and by the subsequent instantaneous passage of the NH$_3$ through the cell membrane, the washing process resulted in H$^+$ remaining inside the cells, which was the cause of the intracellular acidification. This may eventually lead to cell death if it persists long enough.

It was important at this point that the washing buffer was sodium-free (<1 mM) because extracellular sodium ions would lead to an instantaneous recovery of the pH$_i$ through the activity of the cloned NHE isoforms.

It was likewise important for all the buffers used (loading buffer, washing buffer, recovery buffer) not to contain any HCO$_3^-$ ions, because the presence of bicarbonate would lead to activation of interfering bicarbonate-dependent pH$_i$ regulatory systems present in the parental LAP-1 cell line.

The microtiter plates with the acidified cells were then (up to 20 minutes after the acidification) transferred to the FLIPR. In the FLIPR, the intracellular fluorescent dye was excited by light with a wavelength of 488 nm generated by an argon laser, and the measured parameters (laser power, illumination time and aperture of the CCD camera incorporated in the FLIPR) were chosen so that the average fluorescence signal per well was between 30 000 and 35 000 relative fluorescence units.

The actual measurement in the FLIPR started with a photograph being taken by the CCD camera every two seconds under software control. After ten seconds, the recovery of the intracellular pH was initiated by adding 90 µl of recovery buffer (133.8 mM NaCl, 4.7 mM KCI, 1.25 mM MgCl$_2$, 1.25 mM CaCl$_2$, 0.97 mM K$_2$HPO$_4$, 0.23 mM KH$_2$PO$_4$, 10 mM HEPES, 5 mM glucose; pH 7.4 [adjusted with NaOH]) by means of the 96-well pipettor incorporated in the FLIPR.

Positive control wells (100% NHE activity) were those to which pure recovery buffer was added, while negative controls (0% NHE activity) received washing buffer. Recovery buffer with twice the concentration of test substance was added to all the other wells. Measurement in the FLIPR terminated after 60 measurements (two minutes).

The raw data are exported into the ActivityBase program. This program firstly calculates the NHE activities for each tested substance concentration and, from these, the $IC_{50}$ values for the substances. Since the progress of $pH_i$ recovery was not linear throughout the experiment, but fell at the end owing to decreasing NHE activity at higher $pH_i$ values, it was important to select for evaluation of the measurement the part in which the increase in fluorescence of the positive controls was linear.

| Example | NHE1 inhibition $IC_{50}$ [nM] |
| --- | --- |
| 1 | 3.9 |
| 2 | 1.9 |
| 3 | 4.7 |
| 4 | 4675 |
| 5 | 6.4 |
| 6 | 27.1 |
| 7 | 14.5 |
| 8 | 3.7 |
| 9 | 2.1 |
| 10 | 38.8 |
| 11 | 81.5 |

In vivo pharmacokinetics—profiling with the "n in one method"

The exposure data and the half-life were determined as characteristic follows:

Two NHE-1 inhibiotors of the invention (example 1 and example 9) and a known NHE-1 reference subtance (cariporide)

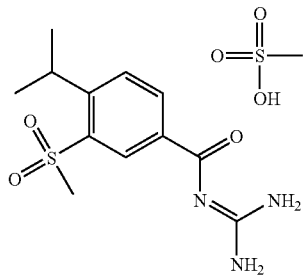

where dissolved in the slightly acidic aqueous medium (water, pH 4, adjusted with 1 M hydrochloric acid). The concentration of the aqueous formulation prepared in this way was about 1.5 mg of each substance per 1 g of solution. 10 ml of this formulation were administered once as bolus by means of a catheter into the jugular vein of a fasting male beagle dog (dose about 1 mg of each administered substance per kg of the dog's body weight). Blood samples were obtained by means of a second catheter after 5 min, 15 min, 30 min, 1 h, 2 h, 4 h, 8 h and 24 h, and heparinized plasma was prepared by centrifugation at 1000 G in appropriate plasma tubes.

The plasma samples were worked up and quantified by MS/MS after an HPLC separation. Simultaneous determination of a plurality of substances was possible with this method owing to its high specificity. The half-lives could be calculated using the WinNonlin computer program from the concentration-time plots (see FIG. 1) and compared with the half-life of the known NHE-1 reference substance. Since the various substances were measured in the same animal at the same time, the result was an accurate comparison of the compounds, and a ranking of the half-lives was possible.

| Compound | Half-life t½ [h] |
| --- | --- |
| Example 1 | 20.2 |
| Example 9 | 39.9 |
| Comparative example cariporide | 4.1 |

It is clearly evident from the concentration-time plots in FIG. 1 and the half-lives found that the compounds of the invention are retained in the blood also over a longer period, and thus the half-lives are 5 to 10 times greater than for the reference substance cariporide.

BREIF DESCRIPTION OF THE DRAWINGS

The captions and signs in the figure were as follows:

FIG. 1: concentration-time plots in the blood plasma of dogs after administration of about 1 mg/kg of example 1, example 9 and cariporide.

Y axis: concentration of the measured compound in µg/ml in the plasma

X axis: time in h

I claim:

1. A compound of formula I or II:

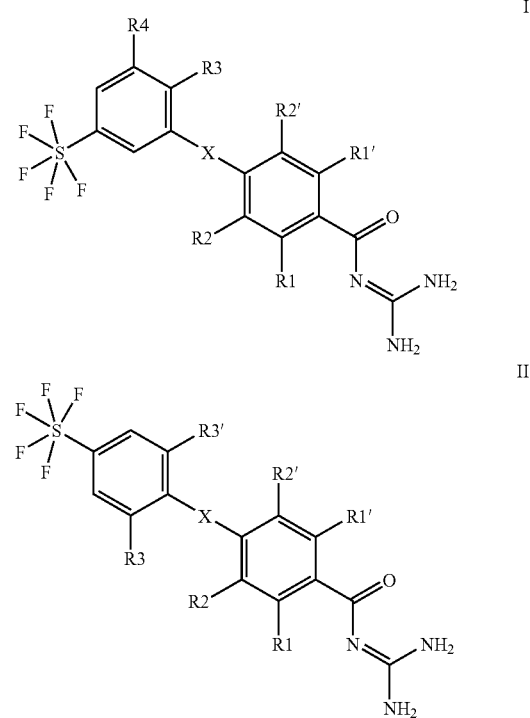

wherein

R1 and R1' are independently of one another hydrogen, alkyl having 1, 2, 3 or 4 carbon atoms, alkoxy having 1, 2, 3 or 4 carbon atoms, F, Cl, Br, I, C, —CN, —NR5R6, —$O_a$—$(CH_2)_b$—$(CF_2)_c$—$CF_3$ or —$(SO_d)_e$—$(CH_2)_f$—$(CF_2)_g$—$CF_3$;

R5 and R6 are independently of one another hydrogen, alkyl having 1, 2, 3 or 4 carbon atoms, or —$CH_2$—$CF_3$;

d zero, 1 or 2;

a, b, c, e, f and g are independently of one another zero or 1;

R2 and R2' are independently of one another hydrogen, F, Cl, Br, I, —CN, —SO$_2$CH$_3$, alkoxy having 1, 2, 3 or 4 carbon atoms, —NR5R6, —O$_a$—(CH$_2$)$_b$—(CF$_2$)$_c$—CF$_3$, —(SO$_h$)$_k$—(CH$_2$)$_l$—(CF$_2$)$_m$—CF$_3$, alkyl having 1, 2, 3, 4, 5 or 6 carbon atoms, cycloalkyl having 3, 4, 5, 6, 7 or 8 carbon atoms wherein 1, 2, 3 or 4 hydrogen atoms of the cycloalkyl are optionally replaced by fluorine atoms, —(CH$_2$)$_n$-phenyl wherein the phenyl is unsubstituted or substituted by 1, 2 or 3 radicals selected from the group consisting of F, Cl, Br, I, —O$_o$—(CH$_2$)$_p$—CF$_3$, alkoxy having 1, 2, 3 or 4 carbon atoms, alkyl having 1, 2, 3 or 4 carbon atoms, and —SO$_2$CH$_3$, or —(CH$_2$)$_q$- heteroaryl wherein the heteroaryl is unsubstituted or substituted by 1, 2 or 3 radicals selected from the group consisting of F, Cl, Br, I, —O$_r$—(CH$_2$)$_s$—CF$_3$, alkoxy having 1, 2, 3 or 4 carbon atoms, alkyl having 1, 2, 3 or 4 carbon atoms, and —SO$_2$CH$_3$;

h is zero, 1 or 2;
k is zero or 1;
l is zero, 1, 2, 3, or 4;
m and o are independently of one another zero or 1;
p is zero, 1, 2 or 3;
n is zero, 1, 2, 3 or 4;
r is zero or 1;
s is zero, 1, 2 or 3;
q is zero, 1, 2, 3, or 4;

R3 and R3' are independently of one another hydrogen, F, Cl, Br, I, —CN, —SO$_2$CH$_3$, alkyl having 1, 2, 3, 4, 5 or 6 carbon atoms, alkoxy having 1, 2, 3, or 4 carbon atoms, or —O$_t$—(CH$_2$)$_u$—CF$_3$;

t is zero or 1;
u is zero, 1, 2 or 3;

R4 is hydrogen, F, Cl, Br, I, —CN, —SO$_2$CH$_3$, NR5R6, —(SO$_v$)$_w$—(CH$_2$)$_x$—(CF$_2$)$_y$—CF$_3$, —O$_z$—(CH$_2$)$_{aa}$—(CF$_2$)$_{bb}$—CF$_3$, alkyl having 1, 2, 3, 4, 5 or 6 carbon atoms, alkoxy having 1, 2, 3 or 4 carbon atoms or cycloalkyl having 3, 4, 5, 6, 7 or 8 carbon atoms, wherein 1, 2, 3 or 4 hydrogen atoms of the cycloalkyl are optionally replaced by fluorine atoms;

v is zero, 1 or 2;
x is zero, 1, 2, 3 or 4;
w, y, z, aa and bb are independently of one another zero or 1;

or

R4 is:
—(CH$_2$)$_{cc}$-phenyl wherein the phenyl is unsubstituted or substituted by 1, 2, or 3 radicals selected from the group consisting of F, Cl, Br, I, —O$_{dd}$—(CH$_2$)$_{ee}$—CF$_3$, alkoxy having 1, 2, 3 or 4 carbon atoms, alkyl having 1, 2, 3 or 4 carbon atoms, and —SO$_2$CH$_3$;

dd is zero or 1;
ee is zero, 1, 2 or 3;
cc is zero, 1, 2, 3 or 4;

or

R4 is:
—(CH$_2$)$_{ff}$-heteroaryl wherein the heteroaryl is unsubstituted or substituted by 1, 2 or 3 radicals selected from the group consisting of F, Cl, Br, I, —O$_{gg}$—(CH$_2$)$_{hh}$—CF$_3$, alkoxy having 1, 2, 3 or 4 carbon atoms, alkyl having 1, 2, 3 or 4 carbon atoms, and —SO$_2$CH$_3$;

gg is zero or 1;
hh is zero, 1, 2 or 3;
ff is zero, 1, 2, 3 or 4;
X is a bond, O, NR7, or S(O)$_{kk}$;
R7 is hydrogen, alkyl having 1, 2, 3 or 4 carbon atoms, —(CH$_2$)$_{mm}$—CF$_3$, or —SO$_2$CH$_3$;
kk is zero, 1 or 2; and
mm is zero, 1, 2 or 3;

where —O$_a$—(CH$_2$)$_b$—(CF$_2$)$_c$—CF$_3$ in the definitions of R1 and R1' and R2 and R2' can be selected independently of one another, and where NR5R6 in the definitions of R1 and R1', R2 and R2' and R4 can be selected independently of one another, or a pharmaceutically acceptable salt thereof.

2. The compound according to claim 1, wherein:

R1 and R1' are independently of one another hydrogen, alkyl having 1, 2, 3 or 4 carbon atoms, methoxy, ethoxy, F, Cl, —NR5R6, —O—CH$_2$—CF$_3$, or —(SO$_d$)$_e$—(CH$_2$)$_f$—CF$_3$;

R2 and R2' are independently of one another hydrogen, F, Cl, —SO$_2$CH$_3$, —(SO$_h$)$_k$—(CH$_2$)$_l$—CF$_3$, alkyl having 1, 2, 3 or 4 carbon atoms, cycloalkyl having 3, 4, 5, 6 or 7 carbon atoms, wherein 1, 2, 3 or 4 hydrogen atoms of the cycloalkyl are optionally replaced by fluorine atoms, phenyl which is unsubstituted or substituted by 1-2 radicals selected from the group consisting of F, Cl, —O$_o$—(CH$_2$)$_p$—CF$_3$, methoxy, ethoxy, alkyl having 1, 2, 3 or 4 carbon atoms, and —SO$_2$CH$_3$, or heteroaryl which is unsubstituted or substituted by 1-2 radicals selected from the group consisting of F, Cl, —O$_r$—(CH$_2$)$_s$—CF$_3$, methoxy, ethoxy, alkyl having 1, 2, 3 or 4 carbon atoms, and —SO$_2$CH$_3$;

R3 and R3' are independently of one another hydrogen, F, Cl, —SO$_2$CH$_3$, alkyl having 1, 2, 3 or 4 carbon atoms, methoxy, ethoxy, or —O$_t$—(CH$_2$)$_u$—CF$_3$, R4 is hydrogen, F, Cl, —SO$_2$CH$_3$, —(SO$_v$)$_w$—(CH$_2$)$_x$—CF$_3$, —O$_z$—(CH$_2$)$_{aa}$—CF$_3$, alkyl having 1, 2, 3 or 4 carbon atoms, methoxy, ethoxy, or cycloalkyl having 3, 4, 5, 6 or 7 carbon atoms, wherein 1, 2, 3 or 4 hydrogen atoms of the cycloalkyl are optionally replaced by fluorine atoms;

x is zero or 1;

or

R4 is phenyl which is unsubstituted or substituted by 1-2 radicals selected from the group consisting of F, Cl, —O$_{dd}$—(CH$_2$)$_{ee}$—CF$_3$, methoxy, ethoxy, alkyl having 1, 2, 3 or 4 carbon atoms, and —SO$_2$CH$_3$;

ee is zero or 1;

or

R4 is heteroaryl which is unsubstituted or substituted by 1-2 radicals selected from the group consisting of F, Cl, —O$_{gg}$—(CH$_2$)$_{hh}$—CF$_3$, methoxy, ethoxy, alkyl having 1, 2, 3 or 4 carbon atoms, and —SO$_2$CH$_3$;

hh is zero or 1;
X is a bond, O, NR7, or S(O)$_{kk}$; and
R7 is hydrogen, alkyl having 1, 2, 3 or 4 carbon atoms, —CH$_2$—CF$_3$ or —SO$_2$CH$_3$.

3. The compound according to claim 1, wherein
R1 and R1' are independently of one another hydrogen, alkyl having 1, 2, 3 or 4 carbon atoms, methoxy, ethoxy, F, Cl, —NR5R6, —O—CH$_2$—CF$_3$, or —(SO$_d$)$_e$—(CH$_2$)$_f$—CF$_3$;

R2 and R2' are independently of one another hydrogen, F, Cl, —SO$_2$CH$_3$, —(SO$_h$)$_k$—(CH$_2$)$_l$—CF$_3$, methyl, cycloalkyl having 3, 4, 5, 6 or 7 carbon atoms, wherein 1, 2, 3 or 4 hydrogen atoms of the cycloalkyl are optionally replaced by fluorine atoms, phenyl which is unsubstituted or substituted by a radical selected from the group consisting of F, Cl, —O$_o$—(CH$_2$)$_p$—CF$_3$, methoxy, ethoxy, alkyl having 1, 2, 3 or 4 carbon atoms, and —SO$_2$CH$_3$, or heteroaryl which is unsubstituted or substituted by a radical selected from the group consisting of F, Cl, —O$_r$—(CH$_2$)$_s$—CF$_3$, methoxy, ethoxy, alkyl having 1, 2, 3 or 4 carbon atoms, and —SO$_2$CH$_3$;

l, p, and s are independently of one another zero or 1;

R3 and R3' are independently of one another hydrogen, F, Cl, —SO$_2$CH$_3$, methyl, methoxy, ethoxy, or —O$_t$—(CH$_2$)$_u$—CF$_3$;

u is zero or 1;

R4 is hydrogen, F, Cl, —SO$_2$CH$_3$, —(SO$_v$)$_w$—(CH$_2$)$_x$—CF$_3$, —O$_z$—(CH$_2$)$_{aa}$—CF$_3$, methyl, methoxy, ethoxy, or cycloalkyl having 3, 4, 5, 6 or 7 carbon atoms, wherein 1, 2, 3 or 4 hydrogen atoms of the cycloalkyl are optionally replaced by fluorine atoms;

x is zero or 1;

X is a bond, O, NR7, or S(O)$_{kk}$; and

R7 is hydrogen, methyl, ethyl, —CH$_2$—CF$_3$, or —SO$_2$CH$_3$.

4. The compound according to claim 1, wherein

R1 and R1' are independently of one another hydrogen, methyl, F, Cl, —CF$_3$, or —O—CH$_2$—CF$_3$;

R2 and R2' are independently of one another hydrogen, F, Cl, —SO$_2$CH$_3$, —SO$_2$—CF$_3$, —CF$_3$, or methyl;

R3 and R3' are independently of one another hydrogen, F, Cl, —SO$_2$CH$_3$, methyl, —CF$_3$, or —O—CH$_2$—CF$_3$;

R4 is hydrogen, F, Cl, —SO$_2$CH$_3$, —O—CH$_2$—CF$_3$ or methyl;

X is a bond, O, NR7, or S(O)$_{kk}$; and

R7 hydrogen, methyl, ethyl, —CH$_2$—CF$_3$ or —SO$_2$CH$_3$.

5. The compound according to claim 1, selected from the group consisting of:

N-[5-Methanesulfonyl-2-methyl-4-(3-pentafluorosulfanylphenoxy)benzoyl]guanidine, N-[5-Methanesulfonyl-2-methyl-4-(4-pentafluorosulfanylphenoxy)benzoyl]guanidine, N-[5-Methanesulfonyl-2-methyl-4-(4-pentafluorosulfanylphenylsulfanyl)benzoyl]-guanidine, N-[5-Methanesulfonyl-2-methyl-4-(4-pentafluorosulfanylphenylsulfonyl)benzoyl]-guanidine, N-[5-Methanesulfonyl-2-methyl-4-(3-pentafluorosulfanylphenylamino)benzoyl]-guanidine, N-[5-Methanesulfonyl-2-methyl-4-(4-pentafluorosulfanylphenylamino)benzoyl]-guanidine, N-{5-Methanesulfonyl-2-methyl-4-[methyl-(3-pentafluorosulfanylphenyl)-amino]benzoyl}guanidine, N-{5-Methanesulfonyl-2-methyl-4-[methyl-(4-pentafluorosulfanylphenyl)-amino]benzoyl}guanidine, N-(2-Methanesulfonyl-5-methyl-4'-pentafluorosulfanylbiphenyl-4-carbonyl)guanidine, N-(2-Methanesulfonyl-5-methyl-3'-pentafluorosulfanylbiphenyl-4-carbonyl)guanidine, and N-(2-Methanesulfonyl-5,2'-dimethyl-4'-pentafluorosulfanylbiphenyl-4-carbonyl)-guanidine.

6. A process for preparing the compound according to claim 1, wherein X is oxygen, said process comprising the steps of:

a) reacting a phenol of formulae III or IV with an aromatic compound of formula V to give a compound of formulae VIa or VIIa, and b) reacting the compound of formulae VIa or VIIa with guanidine to give an acylguanidine of formulae Ia or IIa,

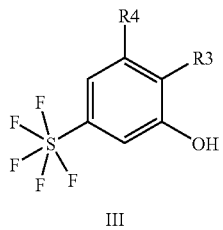

III

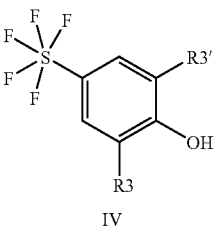

IV

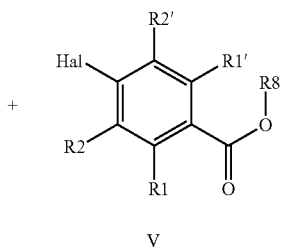

V

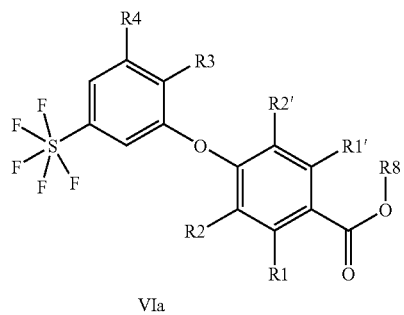

VIa

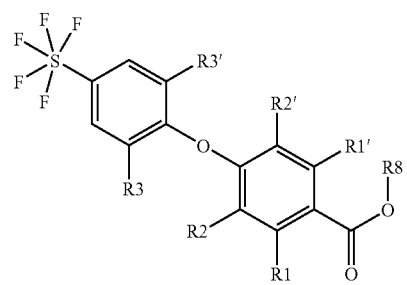

VIIa

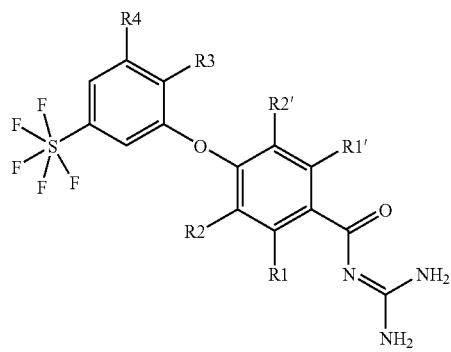

Ia

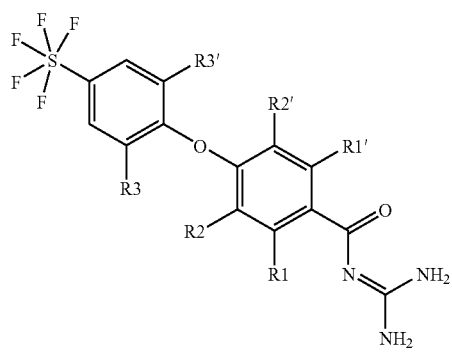

IIa wherein R1, R1', R2, R2', R3, R3' and R4 have the meaning indicated in claim 1, Hal is F, Cl, Br or I, and R8 is hydrogen or alkyl having 1, 2, 3 or 4 carbon atoms.

7. A process for preparing the compound according to claim 1, wherein X is NR7, said process comprising the steps of:

a) sulfonating an aniline of formulae VIII or IX with a sulfonyl chloride to give a compound of formulae X or XI, b) reacting the compound of formulae X or XI with an aromatic compound of formula V to give a compound of formulae VIb or VIIb, c) derivatizing the compound of the formulae VIb or VIIb to prepare a compound of formulae VIb/c or VIIb/c wherein R7 has the meaning indicated in claim 1 except for hydrogen and d) reacting the compound of the formulae VIb/c or VIIb/c with guanidine to give an acylguanidine of formulae Ib or IIb

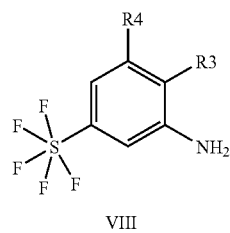

VIII

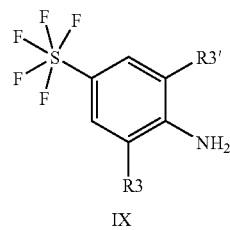

IX

-continued
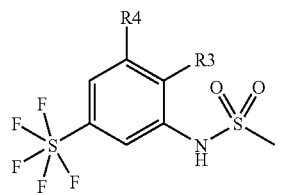
X
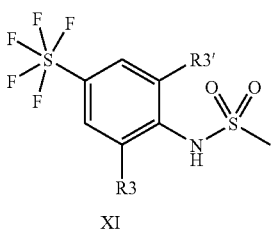
XI
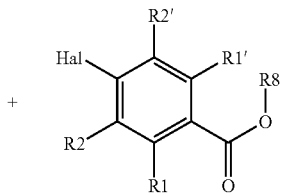
V
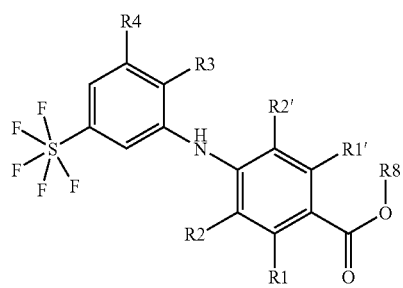
VIb
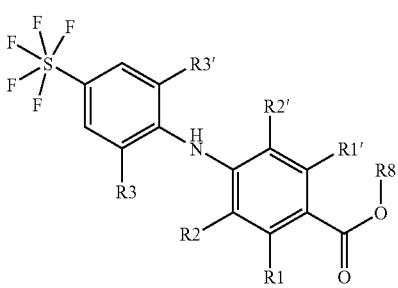
VIIb
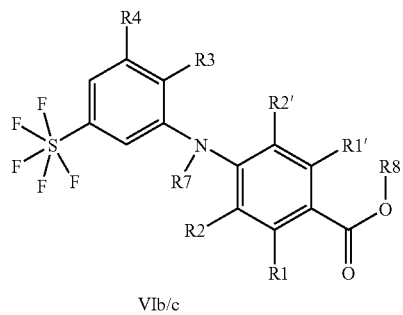
VIb/c
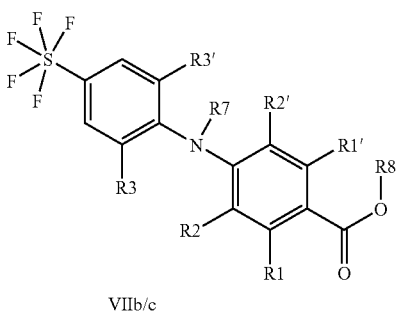
VIIb/c
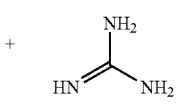

-continued

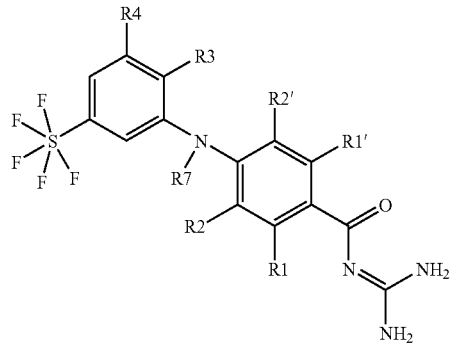

Ib

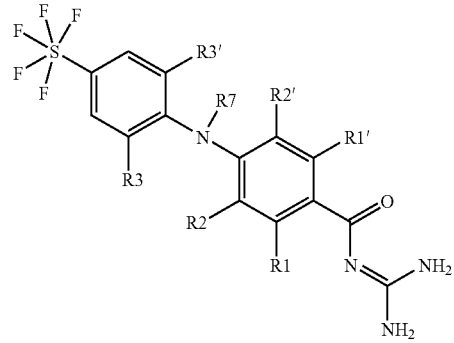

IIb wherein R1, R1', R2, R2', R3, R3', and R4 have the meaning indicated in claim 1, Hal is F, Cl, Br or I, and R8 is hydrogen or alkyl having 1, 2, 3 or 4 carbon atoms.

8. A process for preparing the compound according to claim 1, wherein X is $S(O)_{kk}$, said process comprising the steps of:

a) reacting a thiophenol of formulae XII or XIII with an aromatic compound of formula V to give a compound of formulae VIe or VIIe,
b) oxidizing the compound of formulae VIe or VIIe to prepare a compound of formulae VIe/f or VIIe/f wherein kk is 1 or 2, and
c) reacting the compound of the formulae VIe/f or VII/ef with guanidine to give an acylguanidine of formulae Ic or IIc,

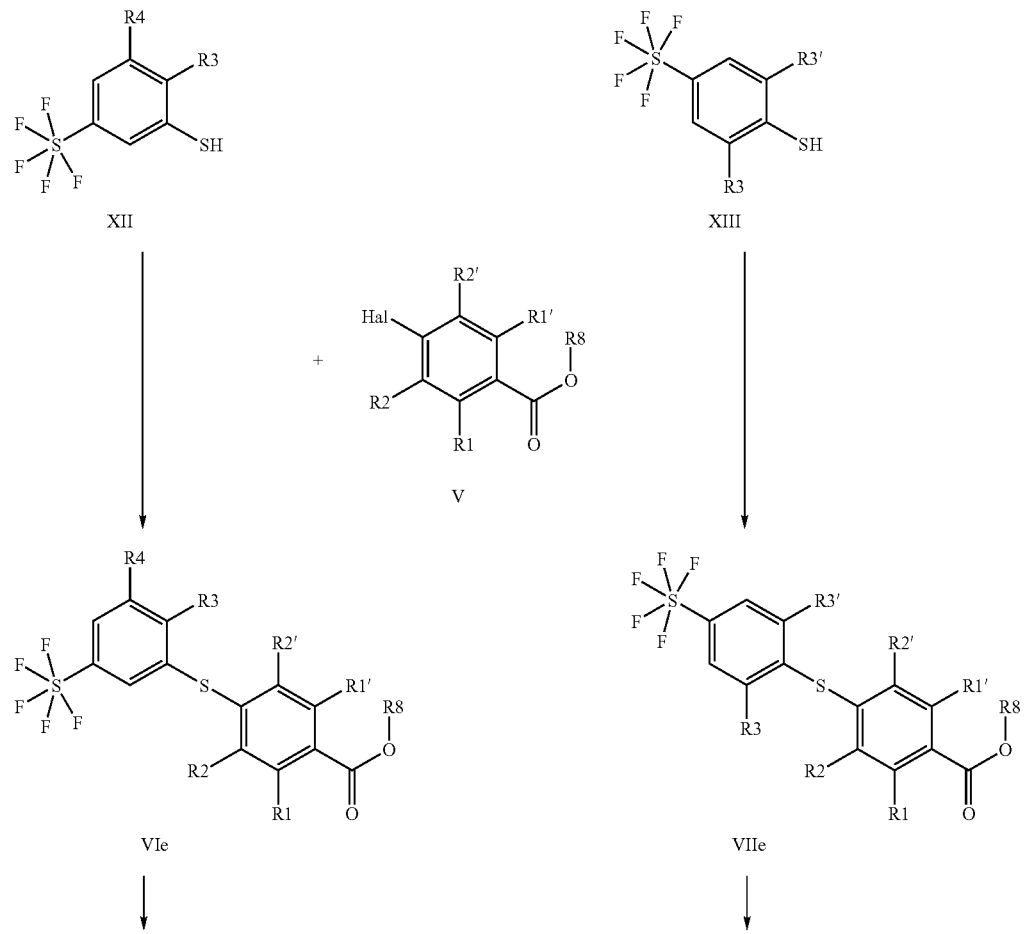

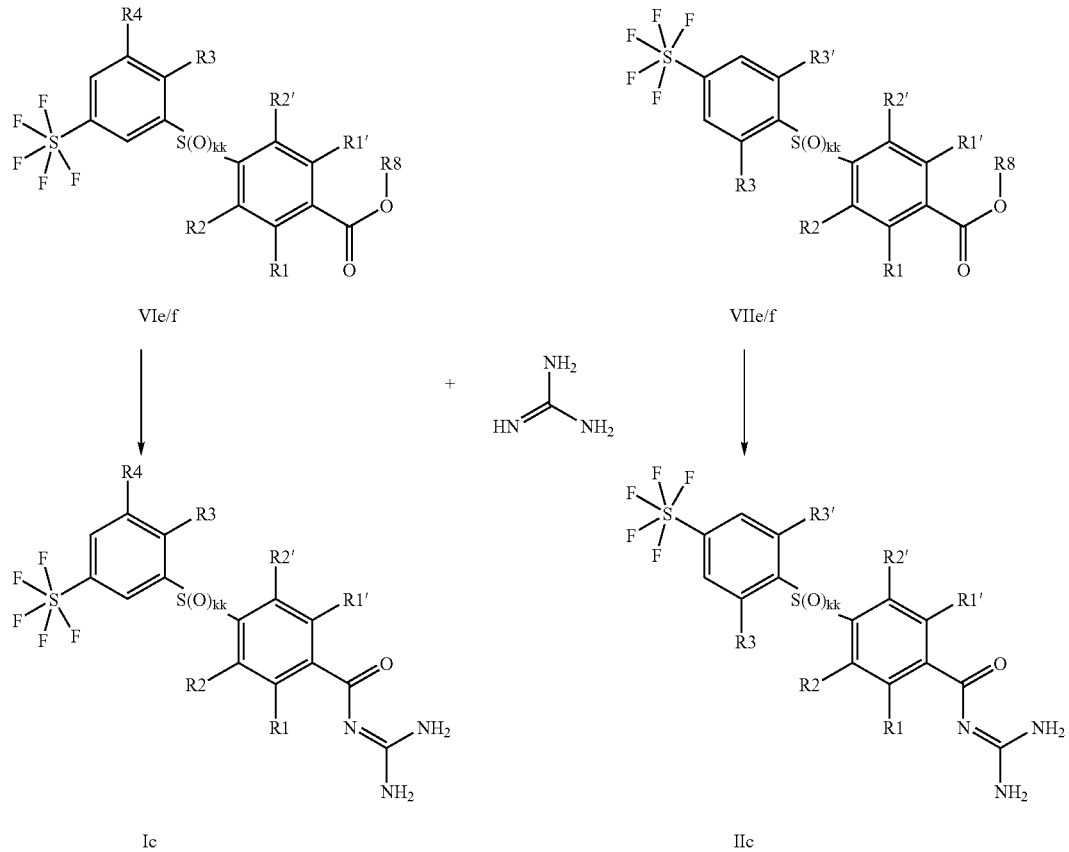

wherein R1, R1', R2, R2', R3, R3', and R4 have the meaning indicated in claim 1, Hal is F, Cl, Br or I, and R8 is hydrogen or alkyl having 1, 2, 3 or 4 carbon atoms.

9. A process for preparing a compound according to claim 1, wherein X is a bond, said process comprising the steps of:

a) coupling a compound of formulae XIV or XV in a Suzuki coupling with a compound of formulae Va to give a compound of formulae VIg or VIIg, and b) reacting the compound of formulae VIg or VIIg with guanidine to give an acylguanidine of formulae Id or IId,

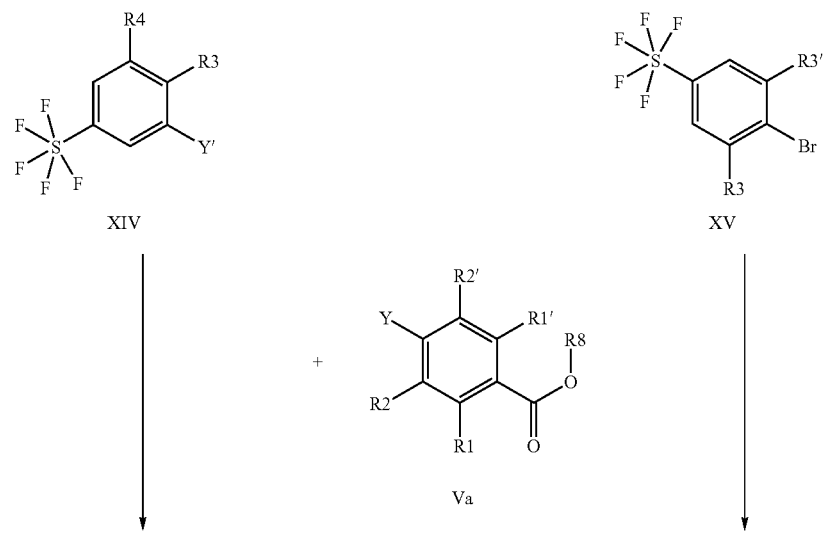

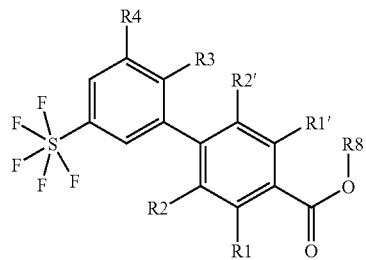

VIg

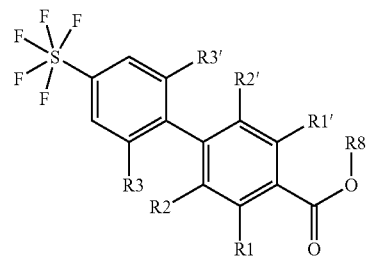

VIIg

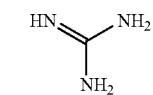

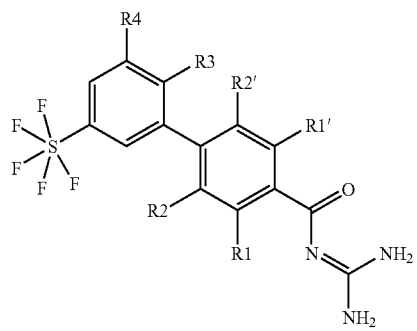

Id

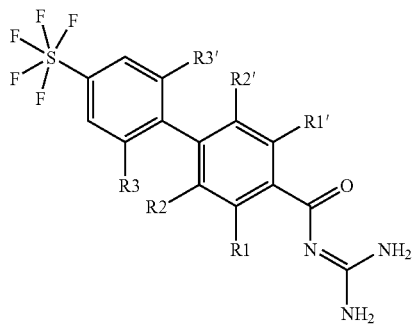

IId wherein R1, R1', R2, R2', R3, R3' and R4 have the meaning indicated in claim 1, Y and Y' are independently of one another Cl, Br or I, and

R8 is hydrogen or alkyl having 1, 2, 3 or 4 carbon atoms.

10. A pharmaceutical composition comprising an effective amount of the compound according to claim 1 or pharmaceutically acceptable salt thereof together with a pharmaceutically acceptable carrier or additive.

* * * * *